US009144249B2

(12) United States Patent
Jolly

(10) Patent No.: US 9,144,249 B2
(45) Date of Patent: Sep. 29, 2015

(54) ENZYMATIC METHODS OF FLAVOR MODIFICATION

(75) Inventor: James F. Jolly, Saint Charles, IL (US)

(73) Assignees: AMANO ENZYME USA, LTD., Elgin, IL (US); AMANO ENZYME, INC., Naku-ku, Nagoya (JP)

( * ) Notice: Subject to any disclaimer, the term of this patent is extended or adjusted under 35 U.S.C. 154(b) by 1109 days.

(21) Appl. No.: 12/488,731

(22) Filed: Jun. 22, 2009

(65) Prior Publication Data

US 2010/0062109 A1    Mar. 11, 2010

Related U.S. Application Data

(60) Provisional application No. 61/129,391, filed on Jun. 23, 2008.

(51) Int. Cl.

| | |
|---|---|
| *A23C 19/032* | (2006.01) |
| *A23L 1/226* | (2006.01) |
| *A23C 19/06* | (2006.01) |
| *A23L 1/22* | (2006.01) |
| *A23L 1/23* | (2006.01) |
| *A23C 19/00* | (2006.01) |
| *C12N 9/16* | (2006.01) |

(52) U.S. Cl.
CPC ........... *A23L 1/22692* (2013.01); *A23C 19/063* (2013.01); *A23L 1/22091* (2013.01); *A23L 1/2305* (2013.01); *C12Y 301/01003* (2013.01); *C12Y 302/01023* (2013.01)

(58) Field of Classification Search
CPC ................. A23C 19/063; C12Y 302/01023; A23L 1/22091; A23L 1/2305
USPC ............................................................ 426/35
See application file for complete search history.

(56) References Cited

U.S. PATENT DOCUMENTS

| | | | |
|---|---|---|---|
| 3,816,259 A * | 6/1974 | Collinge et al. ............. | 435/207 |
| 5,902,617 A | 5/1999 | Pabst | |
| 6,007,851 A | 12/1999 | Schoenmaker et al. | |
| 2002/0081352 A1 | 6/2002 | Rhode, Jr. et al. | |
| 2004/0156970 A1* | 8/2004 | Kortum et al. ................ | 426/582 |
| 2008/0286412 A1* | 11/2008 | Dekker et al. ................. | 426/42 |
| 2009/0098222 A1* | 4/2009 | Matsuda et al. .............. | 424/725 |

FOREIGN PATENT DOCUMENTS

| | | |
|---|---|---|
| EP | 1 915 913 A1 | 4/2008 |
| WO | WO 2006/078615 A2 | 7/2006 |
| WO | WO 2007/060247 A2 | 5/2007 |

OTHER PUBLICATIONS

Kilcawley, K., Enzyme Technology for the Dairy Industry, Food Biotechnology, Second Edition, Taylor and Francis Group, 2006.*
International Search Report issued on Feb. 26, 2010 in application No. PCT/US2009/048104.
Biocatalysts Limited, "The Use of Enzymes for Dairy Flavour Enhancement (including Enzyme Modified Cheese)," www.biocatalysts.com, 2004.

(Continued)

*Primary Examiner* — D Lawrence Tarazano
*Assistant Examiner* — Philip Dubois
(74) *Attorney, Agent, or Firm* — Foley & Lardner LLP

(57) ABSTRACT

Described are enzymatic methods of making food products and modifying food flavor using, for example, a lipase and a lactase, and related enzyme compositions and food products.

13 Claims, 16 Drawing Sheets

(56) References Cited

OTHER PUBLICATIONS

Amano Enzyme Inc., "CheeseMax," Technical Data Sheet, publicly available prior to 2008.
Amano Enzyme Inc., "Lipase M "Amano" 10," Technical Data Sheet, publicly available prior to 2008.
Amano Enzyme Inc., "Lipase A "Amano" 12," Technical Data Sheet, publicly available prior to 2008.
Amano Enzyme Inc., "Lipase DF"Amano" 15-K," Technical Data Sheet, publicly available prior to 2008.
Amano Enzyme Inc., "Lipase R "Amano"," Technical Data Sheet, publicly available prior to 2008.
Amano Enzyme Inc., "β-Galactosidase Biolacta," Technical Data Sheet, publicly available prior to 2008.

* cited by examiner

A

B

C

D

A

B

FIG. 13, cont't.
C
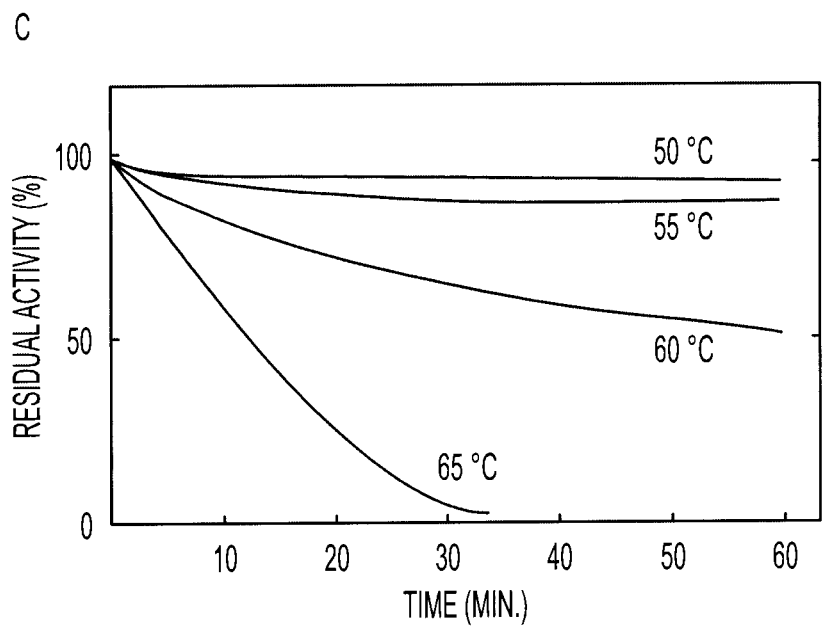
D
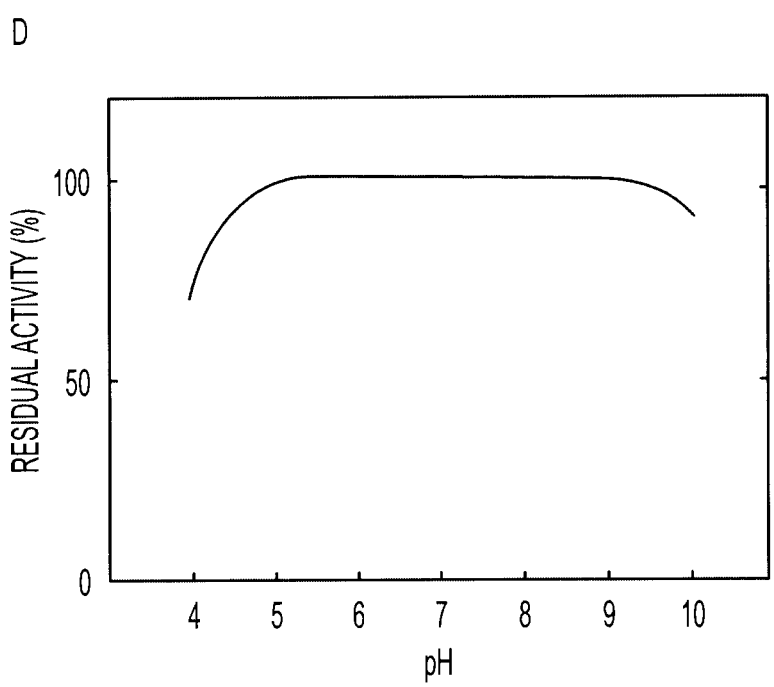

A

B

FIGURE 14, con't.
C
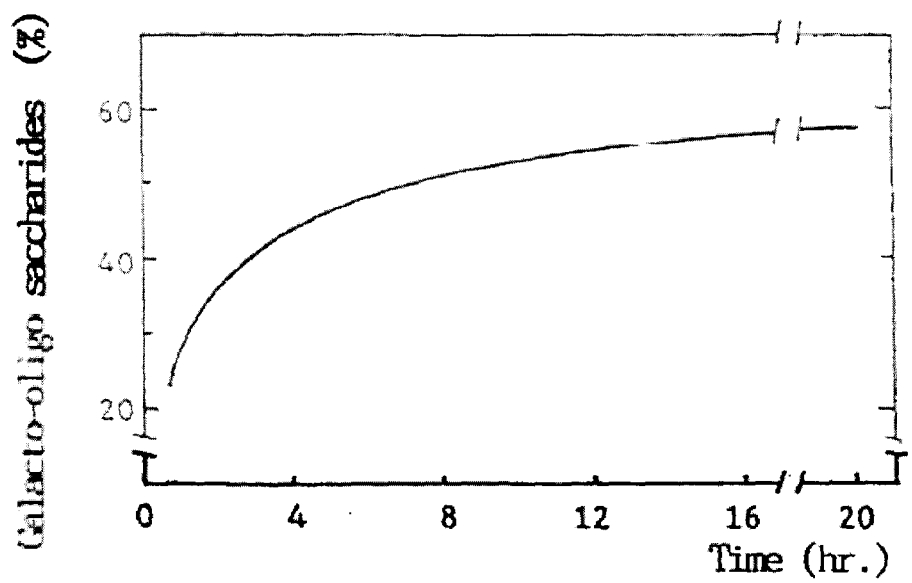

ENZYMATIC METHODS OF FLAVOR MODIFICATION

PRIORITY

This application claims the priority benefits under 35 U.S.C. §119(e) of U.S. Provisional Application No. 61/129,391 filed Jun. 23, 2008, the entire contents of which are incorporated herein by reference in their entirety.

FIELD OF THE INVENTION

Described are enzymatic methods of making food products and modifying food flavor using, for example, a lipase and a lactase, and related enzyme compositions and food products.

BACKGROUND

Enzymes can be used to modify the flavor, texture and aroma of food and beverages. One example of enzyme use in the food industry is found in cheese making. Cheese manufacturers use enzymes to make cheese and enhance flavor. For example the enzyme rennet (a protease) turns milk into curds and whey. Other enzymes turn bland cheese curd into different flavored cheeses. The flavors of most natural cheeses are due to enzymes produced by microflora naturally present in cheese, while the flavors of enzyme modified cheeses (EMCs) are due to enzymes added during the production process.

EMCs are a type of processed cheese produced by adding enzymes, such as lipase and/or protease, to immature cheese to impart desired flavor. EMCs are typically made from young (immature) cheese (such as mild cheese curds) to which enzymes are added to develop the desired cheese flavor in a short time period (e.g., in about 24 hours). The flavor of an EMC can be 10 times as strong as a natural cheese, and depends largely on the enzyme reaction used to produce the EMC. Commercially, EMC is used as a processed cheese product, or as a powder that can be added to other food products to impart a cheese flavor, such as snack chips, soups, etc.

EMCs are commonly produced with lipases. Lipases break down the lipids present in the cheese, releasing fatty acids that impart flavor. For example, the release of high levels of butyric acid imparts "blue" flavor notes to cheese. Different lipases have different fatty acid profiles that result in different flavors.

There remains a need, therefore, for enzymatic methods for producing EMCs with desired flavors.

SUMMARY

In accordance with some embodiments, there is provided a method of preparing a food product comprising contacting a food composition comprising lipids and lactose with one or more lipases and one or more lactases, wherein at least one of the one or more lactases exhibits galactose transferring activity. In some embodiments, at least one of the one or more lipases preferentially hydrolyzes short chain fatty acids before hydrolyzing long chain fatty acids. In some embodiments, the method further comprises adding lactose to the food composition. In some embodiments, the method further comprises an enzyme inactivation step.

In some embodiments, the lipase comprises a lipase EC 3.1.1.3 produced by *Rhizopus oryzae* fermentation, a lipase EC 3.1.1.3 produced by *Mucor javanicus* fermentation, a lipase EC 3.1.1.3 produced by *Aspergillus niger* fermentation, a lipase EC 3.1.1.3 produced by *Penicillium camemberti* fermentation, and/or a lipase EC 3.1.1.3 produced by *Penicillium roqueforti* fermentation.

In some embodiments, the lactase comprises β-galactosidase EC 3.2.1.23 produced by *Bacillus circulans* fermentation.

In some embodiments, the food product has a higher ratio of free short chain fatty acids to free long chain fatty acids than a comparable product treated with the one or more lipases but not the one or more lactases. In some embodiments, the food product has stronger cheese flavor than a comparable product treated with the one or more lipases but not the one or more lactases. In some embodiments, the food product has less of a soapy flavor than a comparable product treated with the one or more lipases but not the one or more lactases.

In some embodiments, the food product is a cheese product selected from enzyme modified cheese and natural cheese. In some embodiments, the food product is a final food product. In some embodiments, the food product is a food additive.

In accordance with other embodiments, there is provided a food product prepared by a method comprising contacting a food composition comprising lipids and lactose with one or more lipases and one or more lactases, wherein at least one of the one or more lactases exhibits galactose transferring activity. In some embodiments, the food product has a higher ratio of free short chain fatty acids to free long chain fatty acids than a comparable product treated with the one or more lipases but not the one or more lactases. In some embodiments, the food product has stronger cheese flavor than a comparable product treated with the one or more lipases but not the one or more lactases. In some embodiments, the food product has less of a soapy flavor than a comparable product treated with the one or more lipases but not the one or more lactases.

In some embodiments, the food product is a cheese product selected from enzyme modified cheese and natural cheese. In some embodiments, the food product is a final food product. In some embodiments, the food product is a food additive.

In accordance with other embodiments, there is provided an enzyme composition comprising one or more lipases and one or more lactases, wherein at least one of the one or more lipases preferentially hydrolyzes short chain fatty acids before hydrolyzing long chain fatty acids, and at least one of the one or more lactases exhibits galactose transferring activity. In some embodiments, the enzyme composition further comprises a buffer. In some embodiments, the enzyme composition further comprises lactose.

BRIEF DESCRIPTION OF THE DRAWINGS

FIG. 8A shows the relative lipase activity of Lipase M under different pH conditions. FIG. 8B shows the relative lipase activity of Lipase M at different temperatures. FIG. 8C shows the pH stability of Lipase M. The enzyme solution was incubated at the indicated pH for 60 minutes at 37° C. FIG. 8D shows the thermostability of Lipase M. The enzyme solution was incubated at the indicated temperature for 60 minutes.

FIG. 9A shows the relative lipase activity of Lipase A12 under different pH conditions. FIG. 9B shows the relative activity of Lipase Al 2 at different temperatures. FIG. 9C shows the pH stability of Lipase A12. The enzyme solution was incubated at the indicated pH for 60 minutes. FIG. 9D shows the thermostability of Lipase A12. The enzyme solution was incubated at the indicated temperature for 60 minutes.

FIG. 10A shows the relative lipase activity of Lipase DF15 under different pH conditions. FIG. 10B shows the pH stability of Lipase DF15. The enzyme solution was incubated at the indicated pH for 2 hours at 37° C. FIG. 10C shows the relative lipase activity of Lipase DF15 at different temperatures. FIG. 10D shows the thermostability of Lipase DF15. The enzyme solution was incubated at the indicated temperature for 30 minutes at pH 7.

FIG. 11A shows the relative activity of Lipase R under different pH conditions in two different buffers (McIlvaine (citrate/phosphate) buffer, lower line, diamonds; phosphate buffer, upper line, squares). FIG. 11B shows the relative lipase activity of Lipase R at different temperatures. FIG. 11C shows the pH stability of Lipase R in two different buffers (McIlvaine buffer, lower line, diamonds; phosphate buffer, upper line, triangles). A 1% enzyme solution was incubated at the indicated pH for 15 minutes at 30° C. FIG. 11D shows the thermostability of Lipase R. A 1% enzyme solution was incubated at the indicated temperature for 15 minutes at pH 7.0.

FIG. 12A shows the relative lipase activity of Lipase G50 under different pH conditions. FIG. 12B shows the lipase relative activity of Lipase G50 at different temperatures. FIG. 12C shows the pH stability of Lipase G50. FIG. 12D shows the thermostability of Lipase G50.

FIG. 13A shows the relative lactase activity of BIOLACTA™ at different temperatures, on a lactose substrate in 0.1M acetate buffer at pH 6.0, with a 10 minute reaction time. FIG. 13B shows the relative lactase activity of BIOLACTA™ under different pH conditions, on a lactose substrate in Britton Robinson buffer, with a 10 minute reaction time at 40° C. FIG. 13C shows the temperature stability of BIOLACTA™ in 0.1 M acetate buffer at pH 6.0 at the following temperatures (from top to bottom): 50° C., 55° C., 60° C. and 65° C. FIG. 13D shows the pH stability of BIOLACTA™. Reactions were incubated at 30° C. for 60 minutes in Britton Robinson buffer.

FIG. 14A shows the temperature stability of BIOLACTA™ in a 5% (dashed line) and 50% (solid line) lactose solution. The reactions were performed at pH 6.0 and for 60 minutes. FIG. 14B shows the percentage of glucose released by different BIOLACTA™ preparations in a 5% lactose solution. The BIOLACTA™ preparations has the following activities (from top to bottom): 15 LU/g lactose, 10 LU/g lactose, 5 LU/g lactose, 2.5 LU /g lactose and 1.25 LU/g lactose. The reactions were performed at 60° C. at pH 6.0. FIG. 14C shows the synthesis of galactooligosaccharide by BIOLACTA™ on a 55% lactose substrate. The reactions were performed at 60° C. at pH 6.0.

DETAILED DESCRIPTION

Described are enzymatic methods of making food products and modifying food flavor using, for example, a lipase and a lactase, and related enzyme compositions and food products.

As used herein, unless otherwise stated, the singular forms "a," "an," and "the" also include the plural.

As used herein the term "short chain fatty acid" means a fatty acid comprising 4-6 carbons.

As used herein the term "long chain fatty acid" means a fatty acid comprising 14-18 or more carbons.

As used herein the term "medium chain fatty acid" means a fatty acid comprising 8-12 fatty acids.

The terms "food" and "food product" as used herein encompass any food or food product (including beverages and beverage products), and refer to both final food products (e.g., suitable for or sold for consumption) and to semi- and fully-processed products that include one or more additional food ingredients, and to products that are used as additives in other food products. In accordance with specific embodiments, the food and food products described herein include dairy products, such as EMCs.

The enzymatic methods described herein provide methods of making food products and methods of modifying food flavor, such as EMC flavor, using, for example, a lipase and a lactase. Related enzyme compositions comprising, for example, a lipase and a lactase, and food products produced by the described methods also are provided.

I. Methods

As noted above, EMCs are commonly produced with lipases, which break down the lipids (including triglycerides) present in the cheese, releasing fatty acids that impart flavor. The free fatty acid profile of a cheese (the amount and type of free fatty acids) affects the flavor of the cheese, and varies with the specific enzyme used. Butyric acid (a short chain fatty acid with four carbon atoms, C4) is typically a desired fatty acid for cheese products, because it provides an intense cheesy flavor. Animal lipases, such as pre-gastric enzyme (PGE) from bovine or calf sources, preferentially release butyric acid, and have been used in cheese production. However, health concerns surrounding the use of animal-derived enzymes in the production of food for human (or other animal) consumption (such as the risk of contamination by animal viruses or prions) have made the use of PGE less desirable. While there are microbial sources of lipase, typical microbial lipases identified to date release long chain fatty acids, such as palmitic acid (with 16 carbon atoms, C16) and stearic acid (with 18 carbon atoms, C18). These long chain fatty acids impart a soapy flavor, which is typically not desirable.

Figure 1:
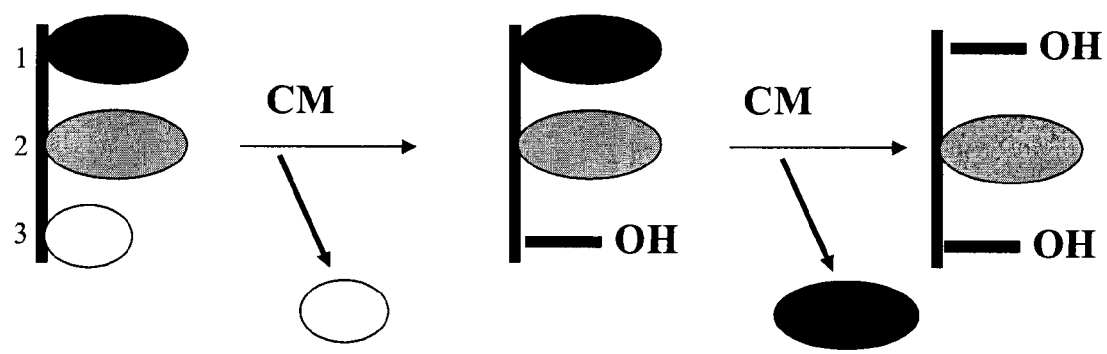
FIG. 1 illustrates the removal of free fatty acids from a lipid by the lipase CHEESEMAX® (CM).

The enzymatic methods described herein use a lipase and a lactase to impart desired flavor to a food product, such as to EMCs. When a typical lipase acts on a typical triglyceride (lipid) present in cheese, the terminal short chain (C4) fatty acid of the triglyceride is released first, followed by the terminal long chain fatty acid, with the middle fatty acid often not being released. This reaction is illustrated in FIG. 1. It has been discovered that by using a lactase in conjunction with a lipase, release of short chain (C4) fatty acids can be achieved with reduced or eliminated release of long chain fatty acids.

Figure 2:
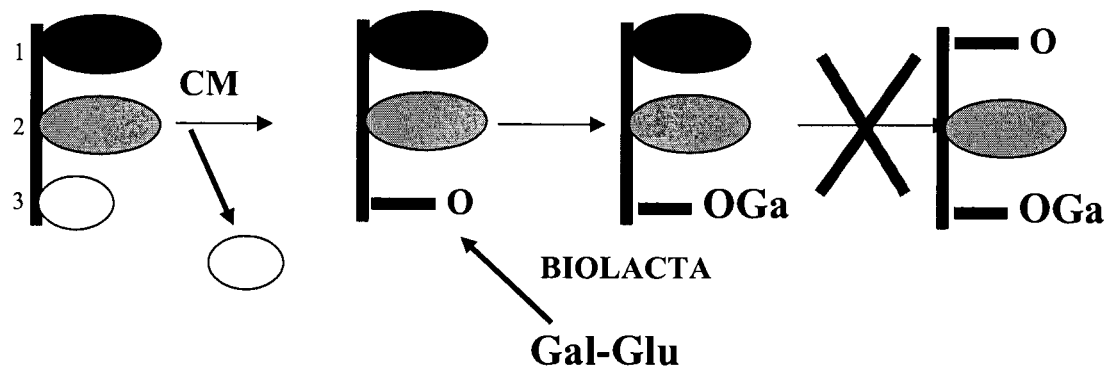
FIG. 2 illustrates the removal of free fatty acids from a lipid by the lipase CHEESEMAX® (CM) and the transfer of galactose to the lipid at the glycerol moiety by BIOLACTA™.

Lactase hydrolyzes lactose into its component sugars, glucose and galactose. Most lactases also have a secondary activity of transferring galactose moieties to another lactose molecule, thus building oligosaccharides. While not wanting to be bound by any theory, it is believed that the use of lactase as described herein transfers a galactose moiety from lactose that is also present in the food product (or that may be added to the food product) to the site of the triglyceride from which the short chain fatty acid was released. Again, while not wanting to be bound by any theory, it is believed that the resulting molecule is not recognized by the lipase, and so is resistant to further hydrolysis that otherwise would have released long chain fatty acids. This reaction scheme is illustrated in FIG. 2.

Not wanting to be bound by any theory, it is believed the enzymatic method described herein proceeds as follows:

Lipase is added to a food composition that comprises lipids and lactose, such as young cheese, cheese curds, or EMC base, and the lipase preferentially releases short chain (e.g., C4) fatty acids from the lipids, producing a desirable cheesy flavor, and leaving a free hydroxyl group on the lipid where the fatty acid was released.

Lactase is added to the food composition and transfers a galactose moiety (from lactose present in and/or added to the composition) to the free hydroxyl position on the lipid, resulting in a molecule that is resistant to further hydrolysis by the lipase.

In some embodiments, lactose is added to the food composition to promote the galactose transfer reaction. For example, lactose may be present in a reaction buffer.

As noted above, this reaction is illustrated in FIG. 2. Also as noted above, the invention is not limited in any way to this mechanism.

In practice, the enzymes (and optional lactose) can be added to the food composition at the same time or sequentially. In some embodiments, the enzymes are added substantially at the same time. In other embodiments, the enzymes are provided in a single composition that is added to the food composition.

The enzymes (and optional lactose) can be added to the food composition by any means, such as by mixing or blending the enzymes with the food composition, or by spraying the enzymes onto the food composition.

In some embodiments, one or more lipases and/or one or more lactases are used. The use of more than one lipase and/or more than one lactase may permit further control over the flavor or production process (e.g., reaction conditions or reaction time). Thus, for example, different lipases and/or different lactases can be used in combination to achieve a desired enzyme activity profile (e.g., a desired lipase activity (including free fatty acid profile), a desired lactase activity, and/or a desired secondary lactase activity).

In some embodiments, the amount of one or more of the enzymes is selected to permit further control over the flavor or production process. For example, the amount of lipase and/or ratio of two or more lipases may be selected to achieve a desired flavor. Additionally or alternatively, the amount of lactase and/or ratio of two or more lactases may be selected to achieve a desired flavor. Indeed the selection of the type and amount of both the lipase(s) and lactase(s) may impact the free fatty acid profile and, thus, impact flavor.

The amount of enzyme used can be expressed in any known means, such as molar amounts or molar ratios (e.g., nanomoles or micromoles of enzyme), weight amounts or weight ratio (micrograms or nanograms of enzyme), or activity amounts or activity ratios (e.g., "units" of enzyme or enzyme activity/weight or mole of enzyme). Standard methods of determining units of lipase and lactase activity are known in the art.

In some embodiments, the methods use an amount of enzymes sufficient to increase the ratio of free small chain fatty acids to long chain fatty acids in the food product, relative to a comparable sample of the same food product that has been treated with lipase but not with lactase.

In some embodiments, the methods use an amount of enzymes sufficient to enhance the flavor of a food product. As noted above, the exact amount of enzymes to be used will vary depending on the nature of the food product, the desired flavor, and the concentration or activity of the enzymes. It should be understood that flavor includes but is not limited to the taste and aroma characteristics of the product. Enhanced flavor can be assessed by conventional means, such as by the use of professional or non-professional taste testers. As noted above, in some embodiments, the methods provide a food product with an enhanced cheesy flavor and/or a reduced soapy flavor.

In some embodiments, the method also includes an inactivation step to inactivate the enzymes. For example, the method may include a heat inactivation step that comprises heating the enzyme-treated food composition for a time and at a temperature that is sufficient to inactivate one or more of the enzymes (or enzyme activities) present in the composition. Suitable inactivation temperatures and times can be readily determined by those skilled in the art. Exemplary temperatures range from about 70° C. to about 90° C. Exemplary times range from about 5 to about 60 minutes, including from about 5 to about 30 minutes. In some embodiments, the inactivation step comprises a pasteurization process, such as is conventional in the art for EMC products. In some embodiments, the inactivation step is selected such that enzyme activity is reduced or eliminated without sacrificing the quality of the food product. However, one advantageous aspect of the methods described herein is that an enzyme inactivation step is not required to prevent development of undesirably soapy flavors that otherwise might arise from the release of long chain fatty acids. Thus, in some embodiments, the methods do not include an enzyme inactivation step.

II. Enzymes

The enzymatic methods described herein can use any enzymes that are safe for use in food production. The enzymes can be obtained from any source, and can be derived from any source, including animal or microbial. For example, the enzymes can be obtained from microorganisms that produce the enzymes naturally or that have been genetically modified to produce one or more enzymes, using methods well known in the art. Enzymes also can be obtained by recombinant methods, such as from transformed or transfected cells, by methods well known in the art. For example, a nucleic acid sequence encoding a desired enzyme can be inserted into an expression vector, which can be used to transform or transfect a host cell for production of the enzyme. Many suitable enzymes are commercially available, as discussed below.

A. Lipases

Lipases (EC 3.1.1.3) are a class of hydrolases that act to hydrolyze the ester bonds of lipid substrates, such as triglycerides. Triglycerides comprise a glycerol molecule esterified with three fatty acids (see e.g., FIGS. 1 and 2). The fatty acids of a triglyceride may be short chain (e.g., comprising 4-6 carbons) or may be medium or long chain (e.g., comprising 8-12 or more carbons). Fatty acid chain lengths of 16, 18, and 20 carbons are the most common in naturally occurring triglycerides. The fatty acids present on a single triglyceride may be the same or different. For example, triglycerides present in dairy products typically include a short chain fatty acid such as butyric acid (C4), and two longer chain fatty acids, such as palmitic acid (C16) and stearic acid (C18).

A number of animal and microbial lipases are known and used in food production, including EMC production, and any of these or other lipases with the desired activity can be used in the methods described herein. In accordance with some embodiments, the lipase preferentially hydrolyzes the short chain fatty acids first, before hydrolyzing longer chain fatty acids. By "preferentially hydrolyzes the short chain fatty acids first" means that the lipase preferentially releases the short chain fatty acid from a lipid before releasing long chain fatty acids, such that the lipase is more likely to release the short chain fatty acid first. FIG. 1 illustrates a lipase systematically hydrolyzing the short chain fatty acid (at position 3 in the figure) of a triglyceride followed by hydrolysis of the longer chain fatty acid (at position 1 in the figure). This desired preferential activity can be confirmed by adding the lipase to a composition comprising triglycerides comprising long chain and short chain fatty acids, stopping the lipase reaction early in the process, before the lipids are completely hydrolyzed, and analyzing the free fatty acid profile (or the remaining partially hydrolyzed triglyceride) to confirm that short chain fatty acids were preferentially released, e.g., that more short chain fatty acids than long chain fatty acids had been released at the time the reaction was stopped. Such an analysis can be undertaken by methods known in the art.

1. CHEESEMAX®

One exemplary lipase that can be used in the methods described herein is sold under the name CHEESEMAX® (Amano Enzyme, U.S., Elgin, Ill.). CHEESEMAX® is sold as a preparation with a lipase activity of not less than 7,500 U/g as assessed by the Food Chemical Codex IV method; one unit is the amount of enzyme that releases 1 µmole of butyric acid in one minute at pH 7.0). CHEESEMAX® is a food grade lipase preparation produced by *Rhizopus oryzae* fermentation under Good Manufacturing Practices.

CHEESEMAX® has a molecular weight of 38,000 and an isoelectric point of 6.8. CHEESEMAX® can be inactivated by heating at 80° C. for about 15 minutes. Some of the characteristics of CHEESEMAX® (temperature and activity, pH and activity, thermostability and pH stability) are shown in FIGS. 4-7. CHEESEMAX® hydrolyzes triglyceride short, medium and long-chain fatty acids with a preference for short and medium chain fatty acids at the 1 and 3 positions of triacylglycerides. Commercial preparations of CHEESEMAX® may be used at the concentration provided, or can be diluted or further concentrated for use. Other lipases produced by *Rhizopus oryzae* fermentation also can be used as described herein.

2. Lipase M

Another exemplary lipase that can be used with the methods described herein is sold under the name Lipase M "Amano" 10 (hereinafter "Lipase M") (Amano Enzyme, U.S., Elgin, Ill.). Lipase M is a food grade lipolytic enzyme preparation produced by *Mucor javanicus* fermentation under Good Manufacturing Practices.

Lipase M can hydrolyze short, medium and long chain fatty acids at 1, 2, and 3 positions of tri- di- and monoglycerides. Lipase M is sold at not less than 10,000 units/gram lipase activity. Commercial preparations of Lipase M may be used at the concentration provided, or can be diluted or further concentrated for use. Some of the characteristics of Lipase M (temperature and activity, pH and activity, thermostability and pH stability) are shown in FIGS. 8A-8D. Other lipases produced by *Mucor javanicus* fermentation also can be used as described herein.

3. Lipase A12

Another exemplary lipase that can be used with the methods described herein is sold under the name Lipase A "Amano" 12 (hereinafter "Lipase A 12") (Amano Enzyme, U.S., Elgin, Ill.). Lipase A12 is a food grade triacylglycerol lipase preparation produced by *Aspergillus niger* fermentation under Good Manufacturing Practices. Lipase A12 can hydrolyze short, medium and long-chain fatty acids at 1, 2, and 3 positions of tri-, di- and monoglycerides. Lipase A12 has a molecular weight of 35,000 and an isoelectric point of 4.10. Lipase A12 is sold at not less than 120,000 units/gram lipase activity. Commercial preparations of Lipase A12 may be used at the concentration provided, or can be diluted or further concentrated for use. Additional characteristics of lipase A12 are shown in FIGS. 9A-D. Other lipases produced by *Aspergillus niger* fermentation also can be used as described herein.

4. Lipase DF15

Another exemplary lipase that can be used with the methods described herein is sold under the name Lipase DF "Amano" 15-K (hereinafter "lipase DF15") (Amano Enzyme, U.S., Elgin, Ill.). Lipase DF15 is produced by *Rhizopus oryzae* fermentation. This food-grade lipase product has a positional specificity for the 1- and 3-positions of glycerides, and hydrolyzes ester bonds of 1(α)- and 3(γ)- positions of triglycerides. Lipase DF15 is relatively specific to fatty acids with long and medium chain length. Lipase activity (by the Food Chemical Codex V method at pH 7) is not less than 150,000 units/gram. Commercial preparations of Lipase DF15 may be used at the concentration provided, or can be diluted or further concentrated for use. Additional characteristics of lipase DF15 are shown in FIGS. 10A-D. Other lipases produced by *Rhizopus oryzae* fermentation also can be used as described herein.

5. Lipase R

Another exemplary lipase that can be used with the methods described herein is sold under the name Lipase R "Amano" (hereinafter "Lipase R") (Amano Enzyme, U.S., Elgin, Ill.). Lipase R is a food grade triacylglycerol lipase produced by *Penicillium roqueforti* fermentation under Good Manufacturing Practices. Lipase R hydrolyzes short-chain and medium-chain fatty acids in preference to long-chain fatty acids from 1 and 3 positions of tri-, di- and monoglycerides. Lipase R has a molecular weight of 25,000, an isoelectric point of 4.50, and inactivation conditions (0.1% enzyme solution) of 60° C. for 2 minutes or 70° C. for 1 minute. Lipase R is sold at not less than 900 units/gram lipase activity. Commercial preparations of Lipase R may be used at the concentration provided, or can be diluted or further concentrated for use. Additional characteristics of lipase R are shown in FIGS. 11A-D. Other lipases produced by *Penicillium roqueforti* fermentation also can be used as described herein.

6. Lipase G50

Another exemplary lipase that can be used with the methods described herein is sold under the name Lipase G "Amano" 50 (hereinafter "Lipase G50") (Amano Enzyme, U.S., Elgin, Ill.). Lipase G50 is a food grade enzyme preparation produced by *Penicillium camembertii* fermentation under Good Manufacturing Practices. Lipase G50 has high esterifying activity and hydrolyzes glycerides, and partial glycerides more rapidly than triglyceride, producing glycerol and fatty acid. Lipase G50R is sold at not more than 50,000 units/gram lipase activity. Commercial preparations of Lipase G50 may be used at the concentration provided, or can be diluted or further concentrated for use. Additional characteristics of lipase G50 are shown in FIGS. 12A-D. Other lipases produced by *Penicillium camembertii* fermentation also can be used as described herein.

B. Lactases

Lactases are another class of hydrolases that hydrolyze the disaccharide lactose into its component monomers, glucose and galactose. As noted above, most lactases also have a secondary activity of transferring galactose moieties to another lactose molecule, and do so repeatedly, thus building oligosaccharides.

A number of animal and microbial lactases are known and used in food production. For example, lactases are added to dairy products to reduce lactose content to make the products more acceptable for people suffering from lactose-intolerance. For example, lactases from *Bacillus circulans, Kluyveromyces fragilis, Kluyveromyces lactis* and *Aspergillus oryzae* are commercially available. Any of these or other lactases with the desired secondary activity can be used in the methods described herein. The desired secondary activity can be confirmed by adding the lactase to a composition comprising lactose and analyzing the resulting oligosaccharide content to confirm that the lactase transferred galactose moieties onto lactose molecules to build oligosaccharides.

In some embodiments, enzymes are selected or engineered to have a high level of the secondary (galactose-transferring). For example, a lactase isolated from *Aspergillus oryza* has been engineered to have high levels of this activity, and is sold under the name BIOLACTA™ (Amano Enzyme, U.S., Elgin, Ill.). BIOLACTA™ is a neutral lactase (β-galactosidase, Nomenclature Committee of the International Union of Biochemistry and Molecular Biology (NC-IUBMB) number: EC3.2.1.23) produced by the controlled fermentation of *Bacillus circulans*.

Figure 13:
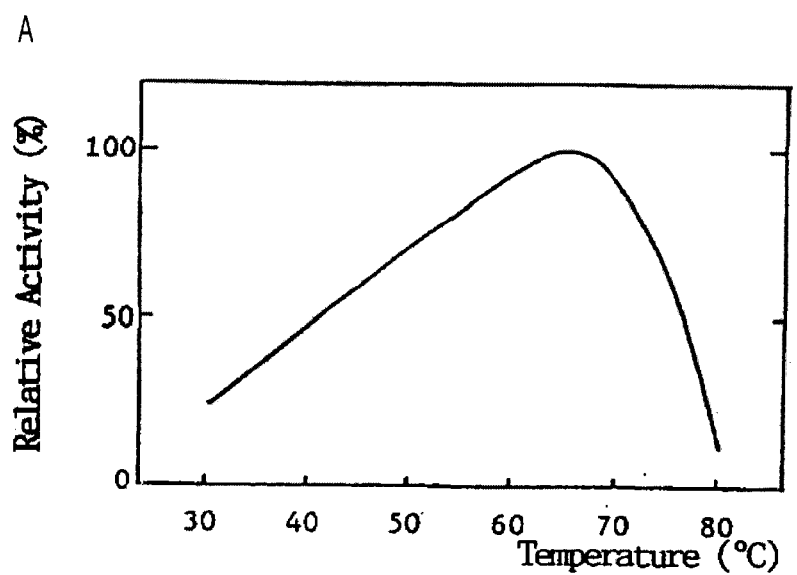
FIGS. 13A-13D are graphs showing different characteristics of BIOLACTA™.
Figure 13:
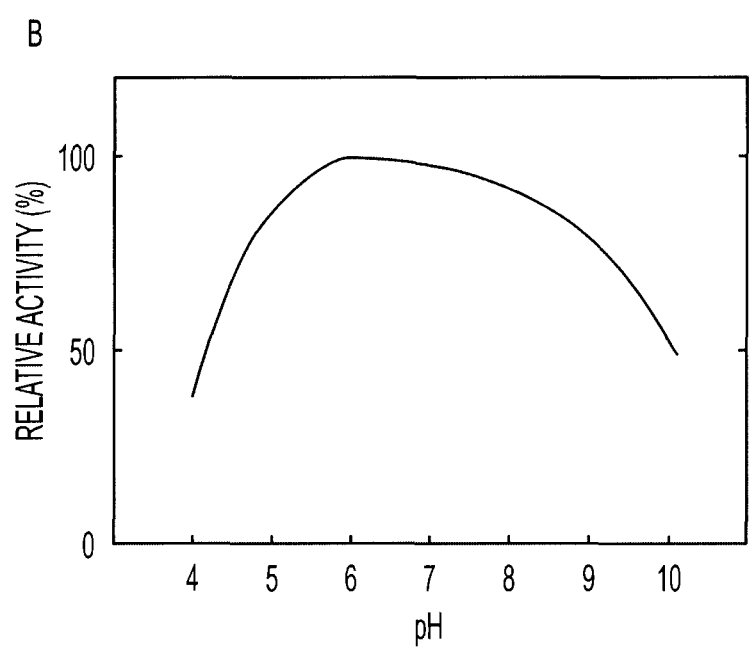
Figure 14:
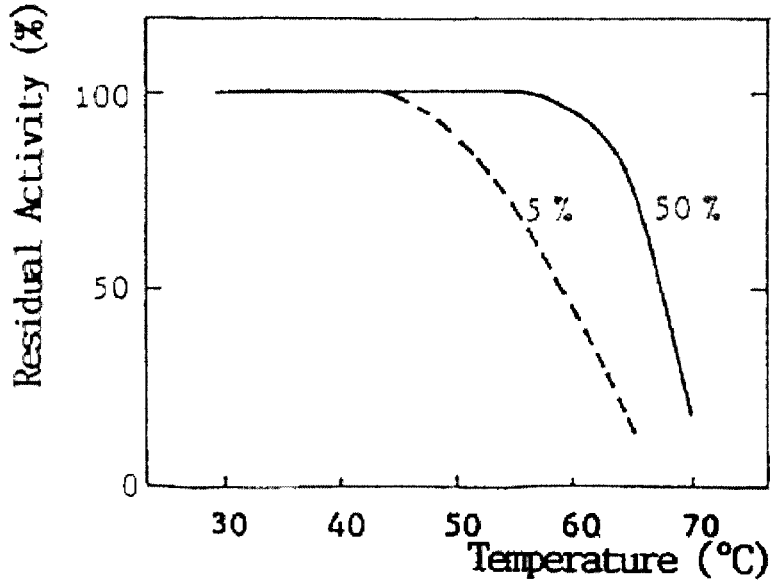
FIGS. 14A-14C are graphs showing different characteristics of BIOLACTA™ in a lactose solution.
Figure 14:
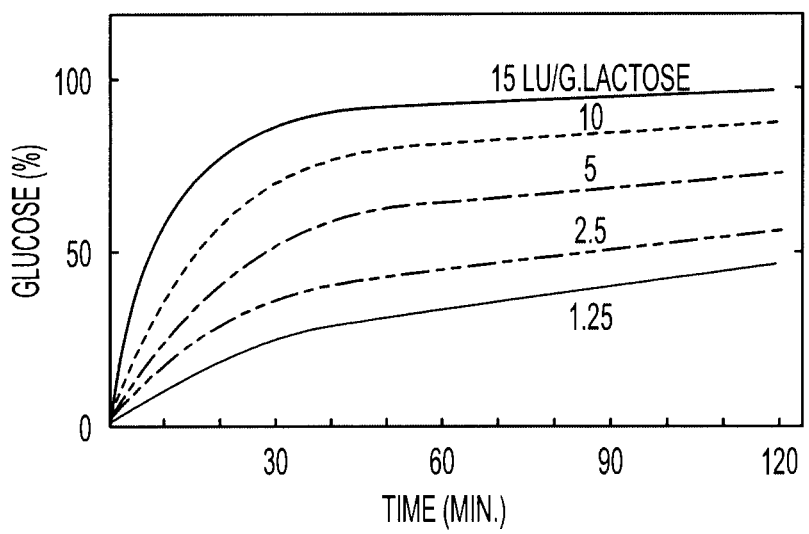

BIOLACTA™ has an optimum pH of about 6.0 (FIG. 13B), is stable at between about pH 5.0-9.5 (FIG. 13D), has an optimum temperature of about 65° C. (FIG. 13A), and is stable for at least an hour at about 55° C. (FIG. 13C). The working temperature of BIOLACTA™ is practically applicable enough at 60° C. in the presence of 50% lactose (FIG. 14A). The hydrolytic speed of BIOLACTA™ (e.g., hydrolysis of lactose in fresh milk) is directly proportional to the amount of BIOLACTA™ added (FIG. 14B). In the presence of 55% lactose, BIOLACTA™ produces oligosaccharide of about 58% including ditri-, tetra- and penta-saccharide (FIG. 14C). One lactose unit (LU) is defined as the amount of enzyme that liberates 1 μmol of glucose per minute at the early stage of the reaction at 40° C. and pH 6.0. BIOLACTA™ is suitable for use in the methods described herein. BIOLACTA™ is sold in commercial preparation with a lactase activity of 5,500 LU/g.

In some embodiments, the lipase used is CHEESEMAX® and the lactase used is BIOLACTA™. For example, about 0.1-0.2% CHEESEMAX® and about 0.1-0.2% BIOLACTA™ can be used. These amounts are exemplary only, and those skilled in the art will recognize that different amounts of different enzymes may be used, depending on enzyme activity and desired affect.

In some embodiments, the lipase comprises a lipase produced by *Rhizopus oryzae* fermentation, a lipase produced by *Mucor javanicus* fermentation, a lipase produced by *Aspergillus niger* fermentation, a lipase produced by *Rhizopus oryzae* fermentation, a lipase produced by *Penicillium camemberti* fermentation, and/or a lipase produced by *Penicillium roqueforti* fermentation, and the lactase comprises β-galactosidase EC3.2.1.23 produced by *Bacillus circulans* fermentation. For example, in some embodiments, the lipase comprises CHEESEMAX®, Lipase M, Lipase A12, Lipase D15, Lipase G50 and/or Lipase R, and the lactase comprises BIOLACTA™. In another specific embodiment, the lipase comprises a lipase produced by *Mucor javanicus* fermentation and the lactase comprises β-galactosidase EC 3.2.1.23 produced by *Bacillus circulans* fermentation, such as where the lipase comprises Lipase M the lactase comprises BIOLACTA™. As noted above, other lactases with galactose-transferring activity can be used in the methods described herein, such as in addition to or instead of BIOLACTA™ in any of the described lipase/lactase combinations.

Other combinations of lipase(s) and lactase(s) can be screened for a desired effect on EMC as illustrated in the examples below. For example, a given combination may have a desired effect on one or more of free fatty acid content, cheesiness, sharpness, lack of soapiness, and aroma.

C. Lactose

In some embodiments, lactose is used to promote the transfer of galactose moieties from lactose molecules to the partially hydrolyzed lipids. Lactose is available commercially from a number of sources, including Sigma Chemical Co.

D. Other Components

The enzymes can be provided in compositions typically used for the purpose of EMC manufacture, which may include, for example, one or more buffers to control pH. For example, if one or more of the enzymes exhibits desired activity at a specific pH or pH range, one or more buffers can be used to control the pH to that range. Exemplary buffers include but are not limited to acetate buffer and phosphate buffer.

Thus, provided here are enzyme compositions comprising one or more lipases and one or more lactases, wherein at least one of the one or more lipases preferentially hydrolyzes short chain fatty acids before hydrolyzing long chain fatty acids, and at least one of the one or more lactases exhibits galactose transferring activity. In some embodiments, the composition further comprises a buffer.

III. Food Products

Also described herein are food products that have been prepared using the enzymatic methods described herein. As noted above, "food products" includes food and beverage products at all stages of production.

Although the particular embodiments and examples that follow use specific food products to illustrate aspects of the invention, it should be understood that the invention is not limited to these specific embodiments, but finds application anywhere where the use of a lipase and a lactase will impart desired flavor to a food product, such as by permitting release of short chain fatty acids while preventing release of long chain fatty acids.

In some embodiments, the food products is a dairy product. Dairy products include but are not limited to milk, cream, ice cream, cheese, cheese curds, butter, buttermilk, yogurt, sour cream, cream cheese, cottage cheese and the like. Dairy products include foods and beverages that are final products and/or that are used as a component of a final product. In accordance with specific embodiments, the food products include EMC prepared using the enzymatic methods described herein. In accordance with other embodiments, the food products include traditional cheese (e.g., hard cheese) prepared using the enzymatic methods described herein.

In some embodiments, the food product is used to impart a dairy flavor to other products, such as a food additive. For example, EMC prepared by the methods described herein can be used to impart a cheesy flavor to snack foods, soups, breads, etc.

In some embodiments, the food products described herein, e.g., prepared by the enzymatic methods described herein, have a free fatty acid content that is different from a comparable food product that has not been prepared by the enzymatic methods described herein, e.g., that has been prepared with lipase only, and not with a lactase that has a secondary (galactose-transferring) activity. Free fatty acid content can be assessed by methods known in the art. Typical methods include extraction of fatty acids from the food product, conversion to methyl esters, and analysis by gas chromatography, as illustrated in the examples below.

Thus, in some embodiments, the food product has a higher ratio of free short chain fatty acids to free long chain fatty acids than a comparable product treated with one or more lipases but not treated with one or more lactases having galactose transferring activity. In some embodiments, the food product has a long chain fatty acid content, such as a C18 fatty acid content, that is about ⅔ or less (e.g., 66% or less, including 63%) than the long chain fatty acid content of a comparable product treated with one or more lipases but not treated with one or more lactases having galactose transferring activity. In some embodiments, the food product has a short chain fatty acid content, such as a C4 fatty acid content, that is about 90% or more (including 91%) of the short chain fatty acid content of a comparable product treated with one or more lipases but not treated with one or more lactases having galactose transferring activity.

In some embodiments, the food product has stronger cheese flavor than a comparable product treated with one or more lipases but not one or more lactases having galactose transferring activity. In some embodiments, the food product has less of a soapy flavor than a comparable product treated with one or more lipases but not one or more lactases having galactose transferring activity.

IV. Examples

The following examples are given to illustrate the present invention. It should be understood, however, that the invention is not to be limited to the specific conditions or details described in these examples.

Examples 1-4 demonstrate that methods described herein result in improved cheese flavor and reduced soapy flavor of EMC. Similar methods can be used to modify the flavor of tradition cheese, but a longer flavor development time would be required for a solid cheese composition (e.g., cheddar cheese) as compared to the liquefied cheese composition used below.

Samples of CHEESEMAX® (LMERE0552501K), and BIOLACTA™ FN5 (P5HA201) were obtained directly from Amano Enzyme USA. All enzymes were used as a 100 mg/ml solution. Weyauwega Star Dairy Cheddar Cheese Curd was purchased from a local grocery store. Valerie acid or C5, an internal standard, was purchased from Aldrich (catalog number 240370); heptadecanoic acid or C17 was purchased from Sigma (H3500).

EXAMPLE 1

Preparation of EMC Using Lipase Alone or Lipase Plus Lactase

This experiment compares EMC prepared using lipase alone or lipase in combination with a lactase with a high level of secondary (galactose-transferring) activity (BIOLACTA™).

Weyauwega Star Dairy Cheddar Cheese Curd was purchased from a local grocery store. About 75 grams (g) of the Cheddar Cheese Curd was weighed into a Cusinart. 75 milliliters (ml) of buffer containing lactose (0.5% w/v lactose, 1.0% w/v NaCl, and 1.5% w/v sodium citrate) was gradually added as the curds were processed into a slurry. Two 50 gram aliquots of the slurry were weighed into sterile polycarbonate flasks, and the samples were then pasteurized for 30 minutes in boiling water. The samples were allowed to cool for 1 hour at 50° C. Both samples were dosed with 2 ml (0.2 grams) of CHEESEMAX® (Amano Enzyme USA), and one of the samples was also dosed with 2 ml (0.2 g) of BIOLACTA™ (Amano Enzyme USA) solution. Both samples were incubated at 50° C. and centrifuged 200 RPM for 21.3 hours. After incubation, both samples were placed in a boiling water bath for 30 minutes to inactivate the enzymes. A small sample (1.05 g) was removed for free fatty acid ("FFA") analysis. The remaining samples were stored in the refrigerator and cooled before taste testing.

EXAMPLE 2

Taste Testing

The samples were each tasted twice. For the first tasting, 2.0 g of the solid part of the samples was weighed into a weighing dish, and the weight was brought to 10.0 g with EASY CHEESE® American Pasteurized Cheese Snack. The sample was mixed thoroughly with a spoon before a single taster tried the sample. Each sample was compared to a control (the EASY CHEESE® alone) and rated on cheesiness and soapiness. Thus, the first taste test focused on qualitative differences. Results are shown below in Table 1.

TABLE 1

Results of Taste Test #1

| Sample | Description of Taste |
| --- | --- |
| Control cheese snack | Bland, not very cheesy |
| CHEESEMAX ® treated EMC | Increased cheesiness (more than other two samples), strong soapiness |
| CHEESEMAX ® + BIOLACTA ™ treated EMC | More cheesy than control (but not as much as CHEESEMAX ® only sample), not as soapy as CHEESEMAX ® only sample |

Before the second tasting, the samples were homogenized for 2 minutes to blend the solid and watery layers. Then, 5.0 g of each sample was weighed into a 50-ml centrifuge tube. 20 g of the pasteurized cheese snack (EASY CHEESE®) was added to each tube and the entire sample was homogenized again for 2 minutes. A single taster tried the samples, smelling each one before tasting it to assess aroma. Each sample was rated on cheesiness, soapiness and aroma on a scale of 1-10, with 10 being the best rating possible. For cheesiness, 10 represents the most flavor; for soapiness, 10 represents the least soapy flavor. A control (EASY CHEESE® alone) was also rated. Results are shown in Table 2, below.

TABLE 2

Results of Taste Test #2

| Sample | Cheesiness | Soapiness | Aroma |
| --- | --- | --- | --- |
| Control cheese snack | 2 | 10 | No cheese smell (0) |
| CHEESEMAX ® treated EMC | 4-5 | 3-4 | Some cheese smell (4) |
| CHEESEMAX ® + BIOLACTA ™ treated EMC | 4-5 | 5-6 | Good cheese smell (6) |

These results show that the EMC treated with lipase and lactase in accordance with the methods described herein had improved flavor and aroma.

EXAMPLE 3

Free Fatty Extraction and Conversion to Methyl Esters

Approximately 1.05 g of each EMC prepared as described above was weighed into a 50 ml centrifuge tube. The following reagents were added to each tube: 1 ml 2.5 M $H_2SO_4$, 3 ml water, and 5 ml internal standard (C5 (valeric acid, purchased from Aldrich, catalog number 240370) and C17 (heptadecanoid acid, purchased from Sigma, catalog number H3500), 1 mg/ml of each fatty acid in 1:1 ether:hexane). Since the EMC was too sticky to emulsify when shaken by hand, each sample was homogenized for one minute with a Polytron PT 1200 E handheld homogenizer at maximum RPM. The samples were centrifuged for 10 minutes at 3000 RPM in a Beckman Coulter Allegra™ 25R Centrifuge, System ID 433500, and then centrifuged again for 20 minutes at 3500 RPM to obtain better separation of layers. The oil layers were drawn off with a pipette and allowed to pass through SEP columns equilibrated with 10 ml heptane. The columns were washed with 10 ml 2:1 chloroform:propanol, and the free fatty acids (FFA) were eluted with 5 ml 2% formic acid in ether. One ml of each elution was transferred to a stoppered glass tube and mixed with 0.2 ml 2,2-dimethoxypropane (Sigma, reagent grade 98%, D136808), 0.2 ml 1.5 M HCl in MeOH, and 0.6 ml anhydrous methanol. The samples were allowed to stand overnight at room temperature before being analyzed on the gas chromatograph.

EXAMPLE 4

Gas Chromatography of Free Fatty Acids

Samples were run on a gas chromatograph system, Model 6890, manufactured by Aglient Technologies, with a split/splitless inlet, a split liner, and a pulsed split inlet model. The split ratio was 50:1 and the split flow 109 ml/min. The inlet temperature was 250° C., and the head pressure was 230 kPa. The column used was 0.15 um DB-23, 60 m×0.25 mm ID. The total gas flow was 113 ml/min, and the carrier gas was helium. Helium flow was 2.2 ml/min, helium make-up flow was 30 ml/min, hydrogen flow was 40 ml/min, and air was 800 ml/min. The average velocity was 34 cm/sec. The oven was programmed as shown below in Table 3, with the detector temperature set at 280° C.:

TABLE 3

Oven Program for FAME analysis

| Temperature (° C.) | Rate (° C./min) | Final Temperature (° C.) | Hold Time (minutes) |
| --- | --- | --- | --- |
| 50 | N/A | 50 | 4 |
| 50 | 25 | 175 | 0 |
| 175 | 4 | 230 | 0 |

Figure 3:
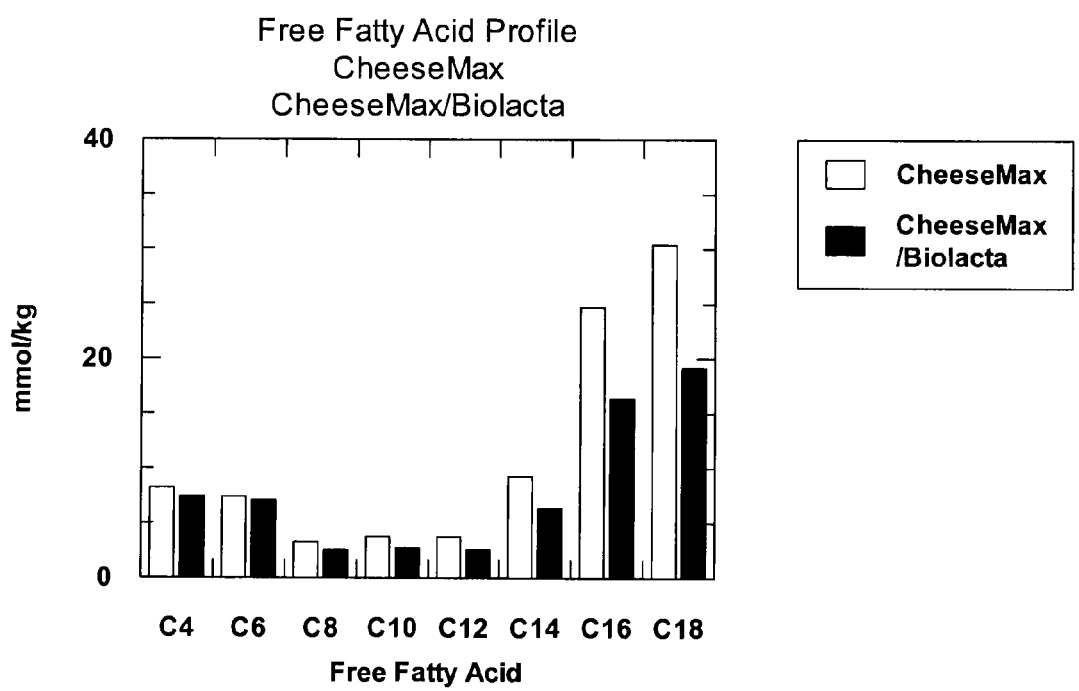
FIG. 3 illustrates the free fatty acid composition of samples after treatment with CHEESEMAX® alone or CHEESEMAX® and BIOLACTA™.
Figure 4:
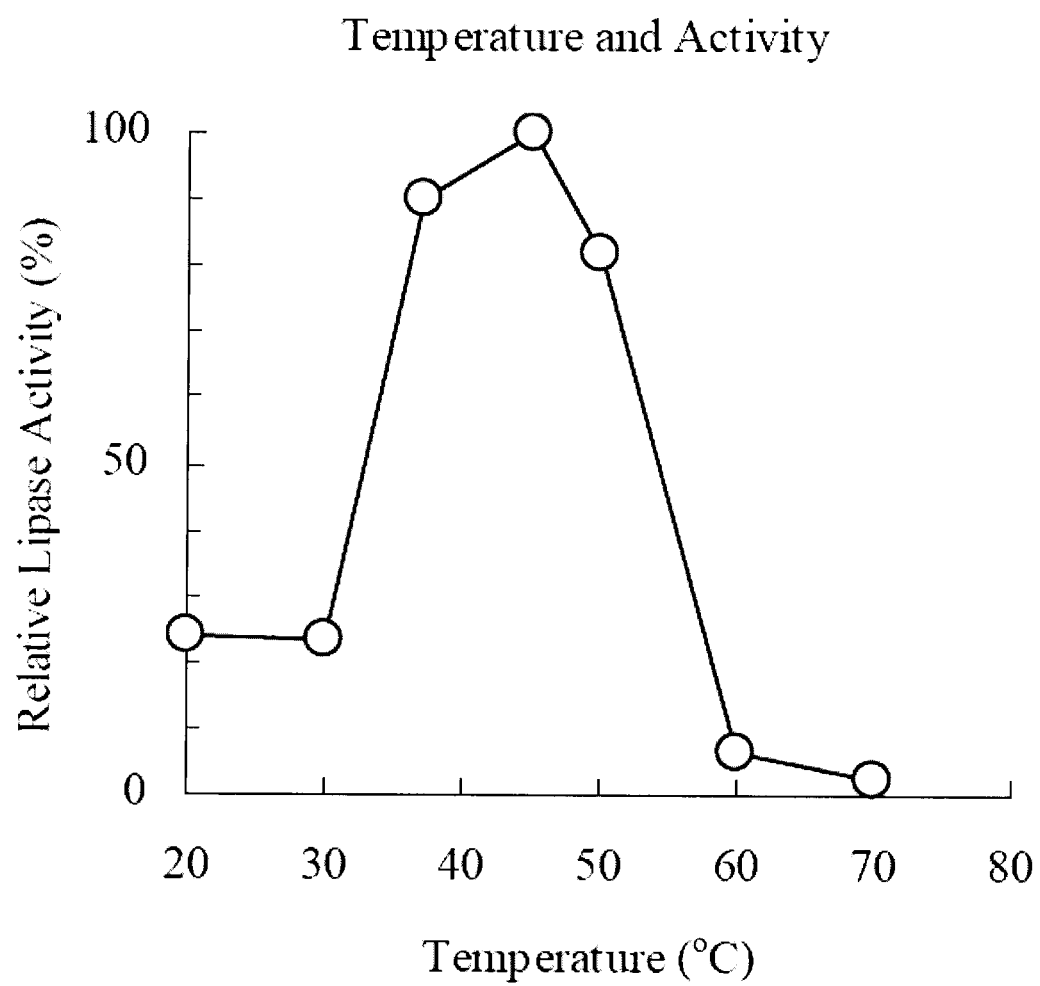
FIG. 4 is a graph showing the relative lipase activity of CHEESEMAX® under different temperature conditions. Reactions were carried out at pH 6.0.
Figure 5:
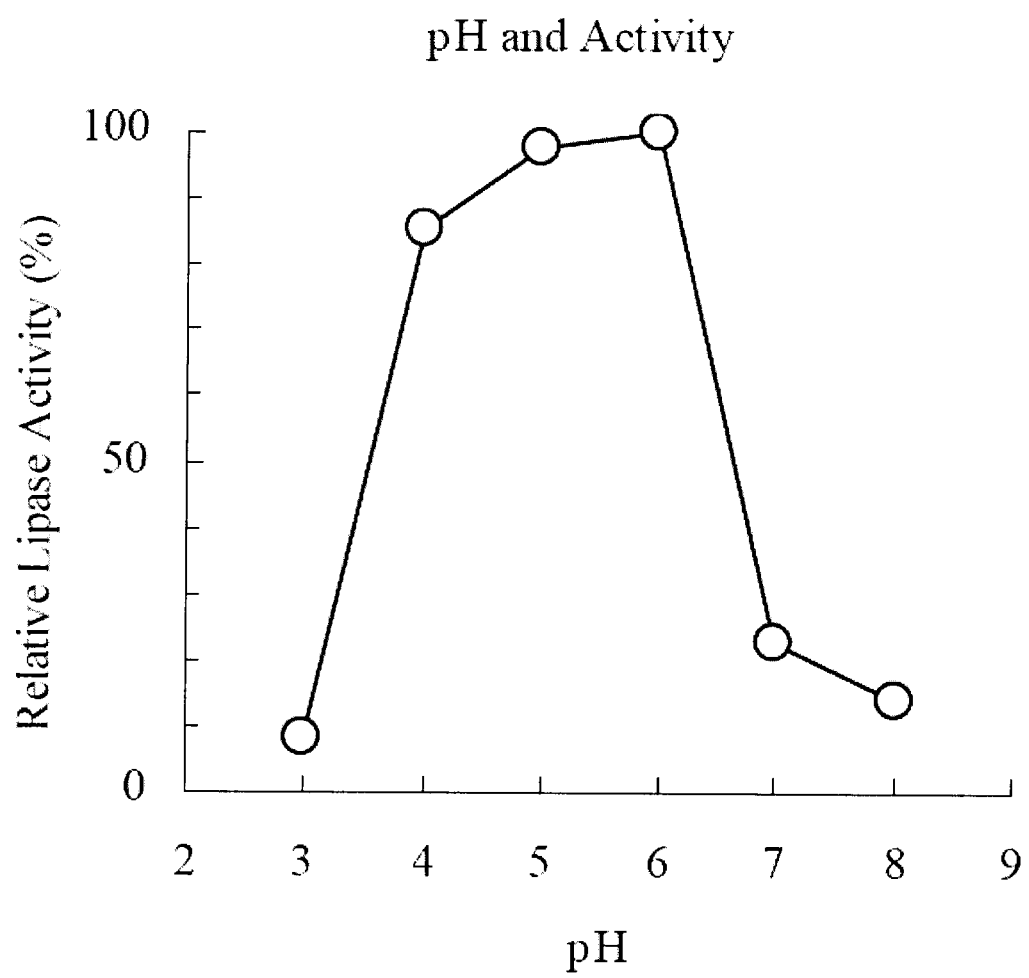
FIG. 5 is a graph showing the relative lipase activity of CHEESEMAX® under different pH conditions. Reactions were carried out at 37° C.
Figure 6:
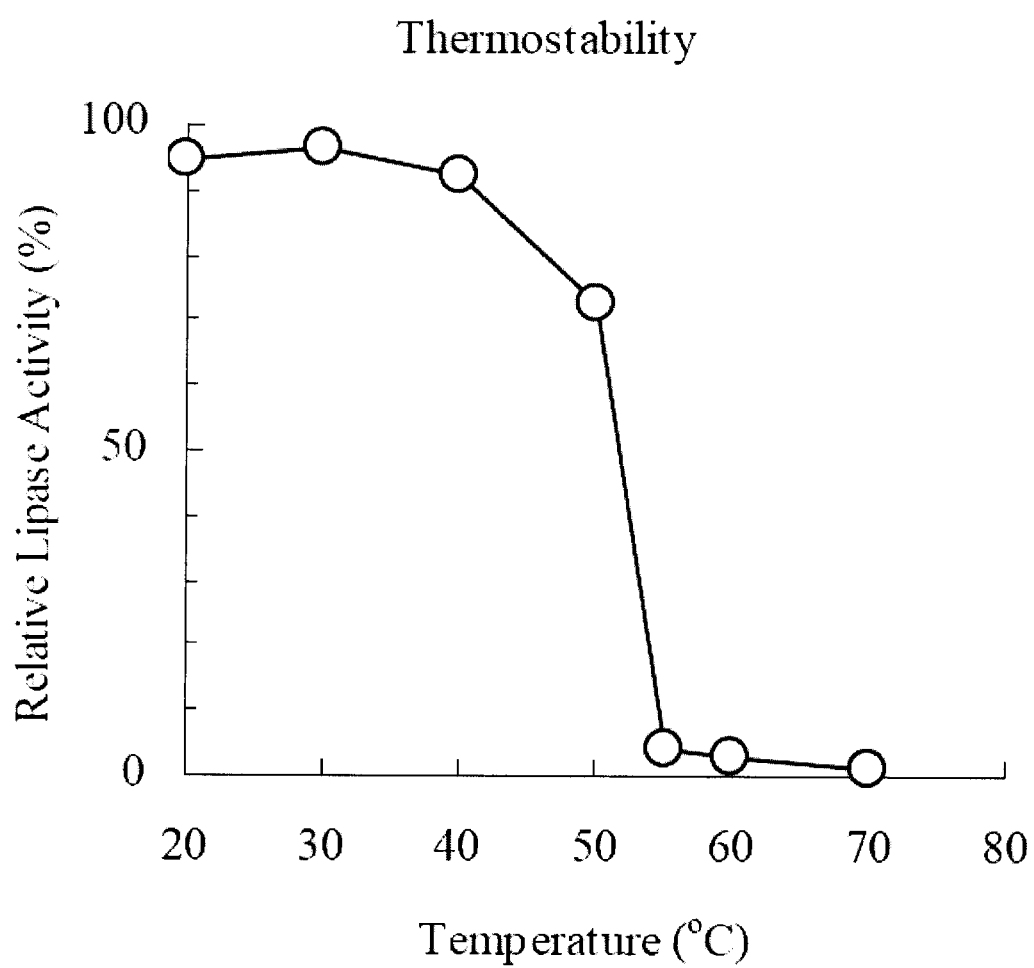
FIG. 6 is a graph showing the thermostability of CHEESE-MAX®. The enzyme solution was incubated at the indicated temperature for 30 minutes at pH 6.0.
Figure 7:
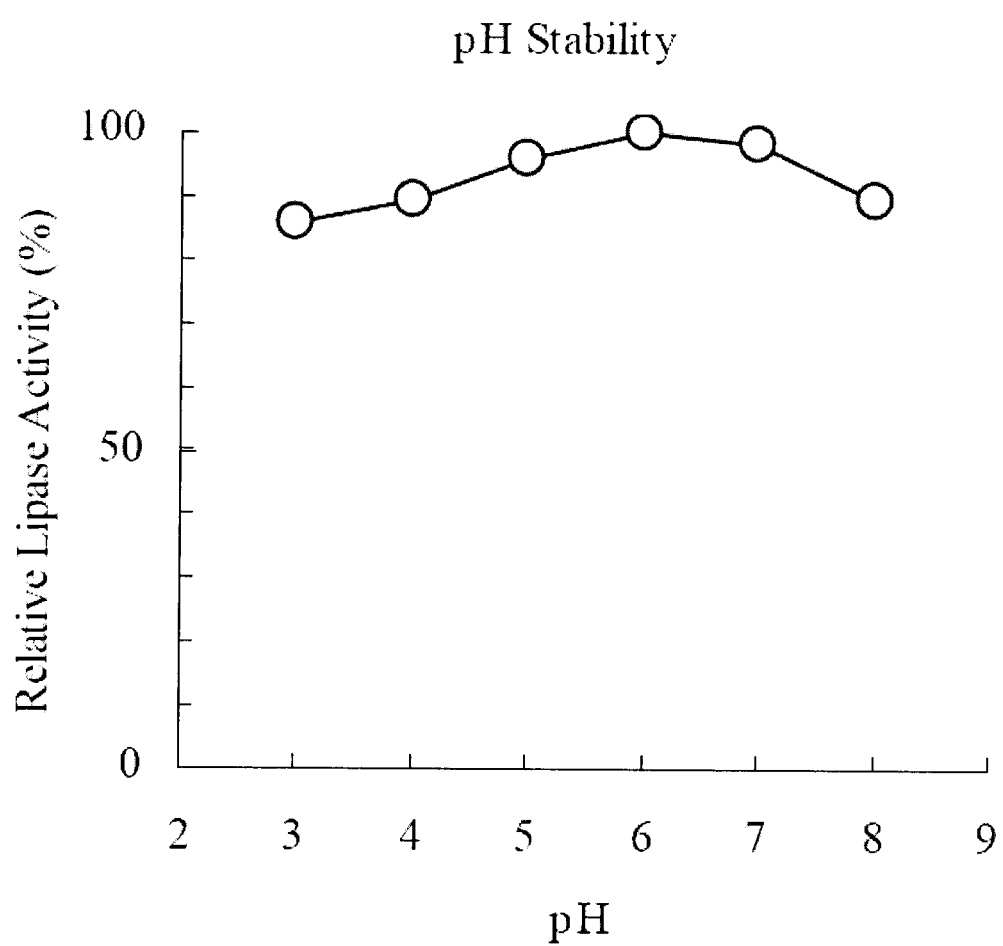
FIG. 7 is a graph showing the pH stability of CHEESE-MAX®. The enzyme solution was incubated at the indicated pH for 60 minutes at 25° C.
Figure 8:
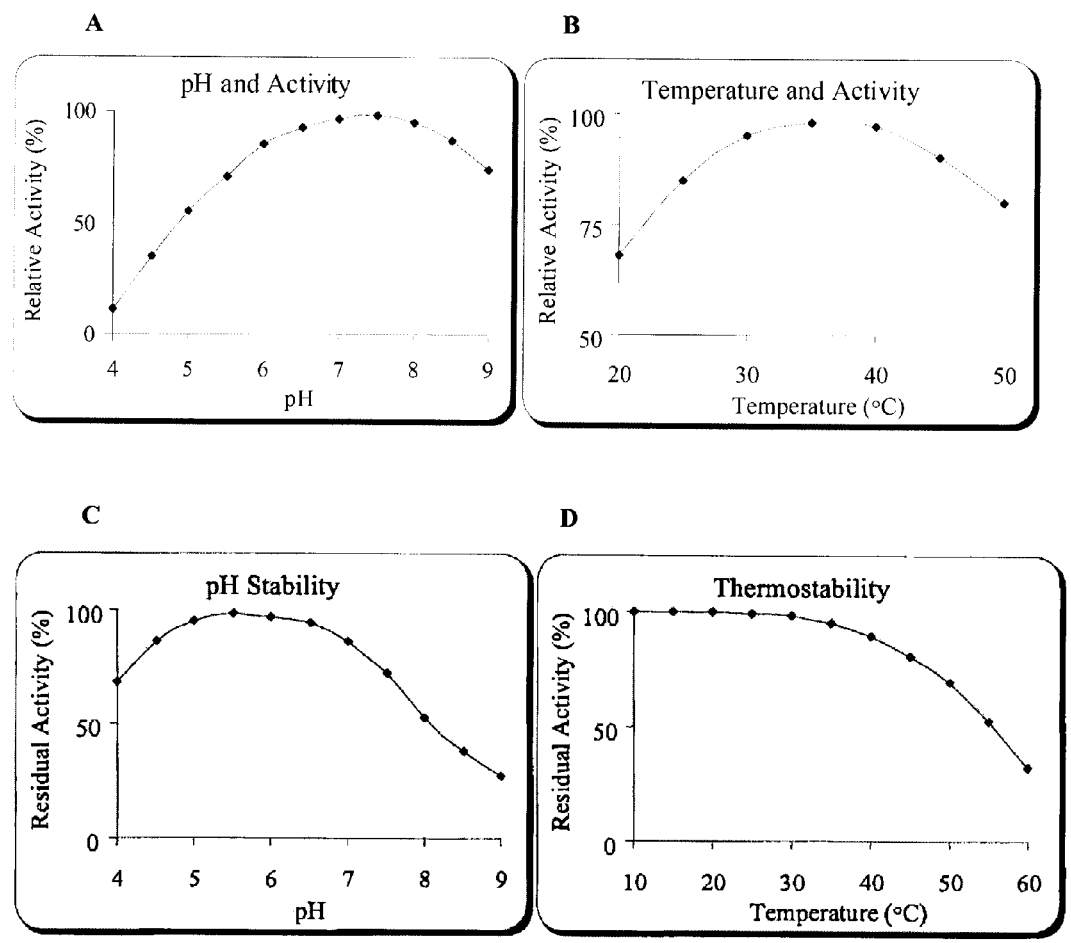
FIGS. 8A-8D are graphs showing different characteristics of Lipase M.
Figure 9:
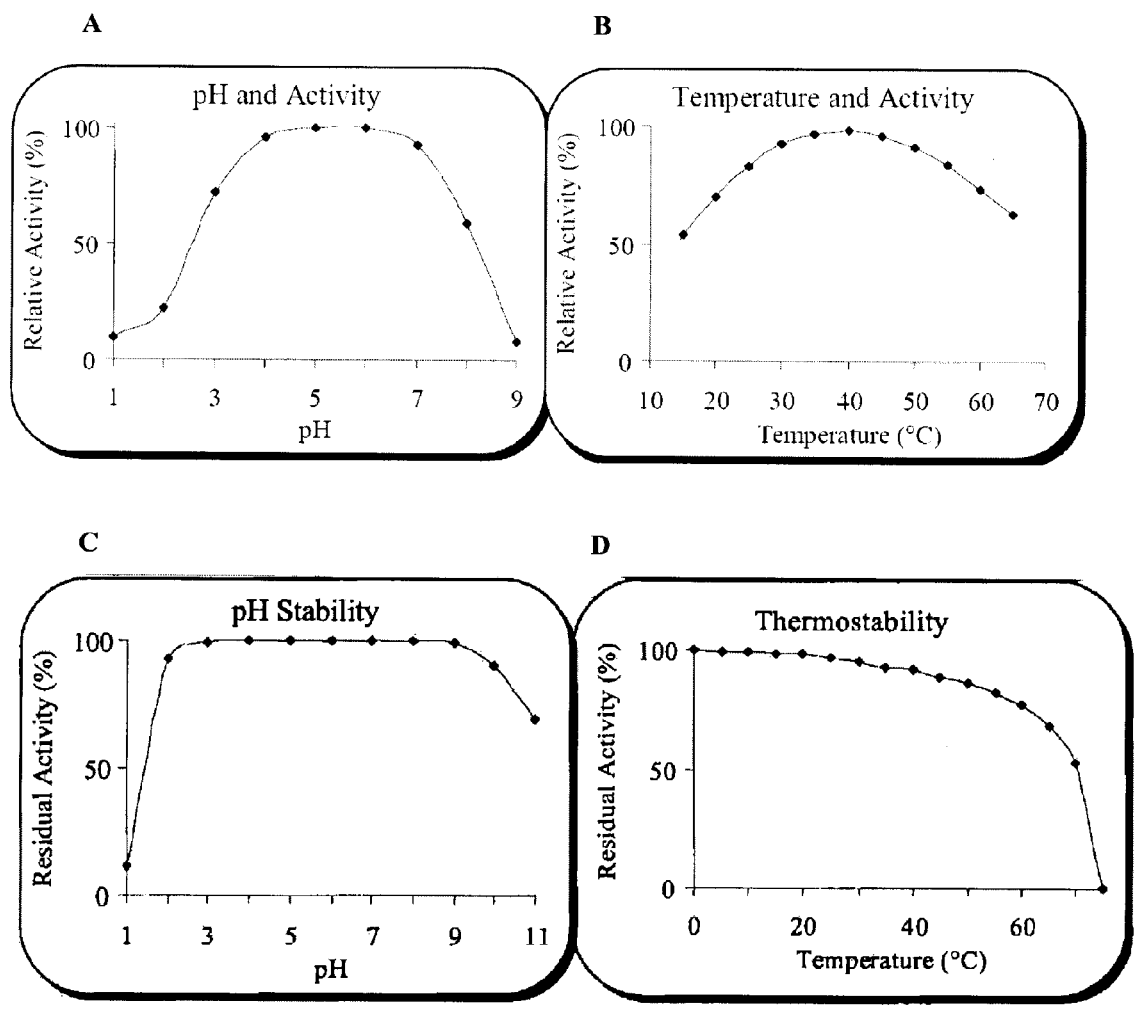
FIG. 9A-9D are graphs showing different characteristics of Lipase A12.
Figure 10:
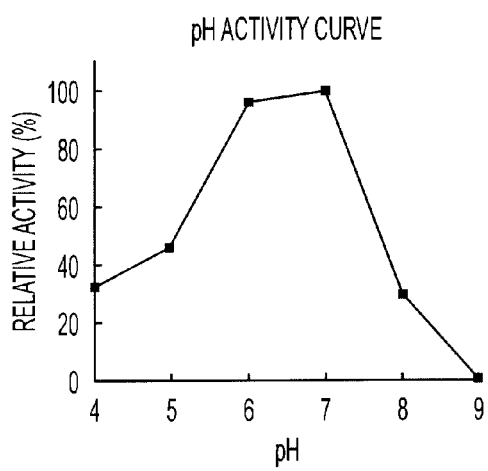
FIG. 10A-10D are graphs showing different characteristics of Lipase DF15.
Figure 10:
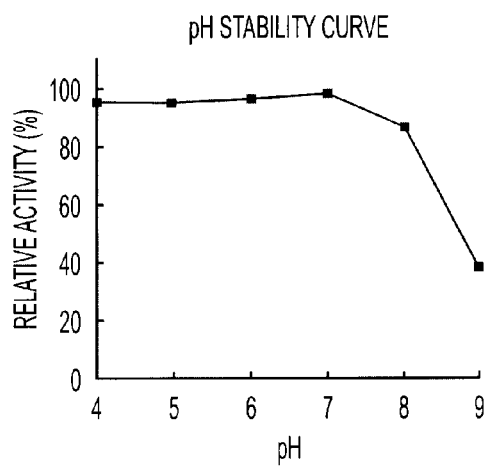
Figure 10:
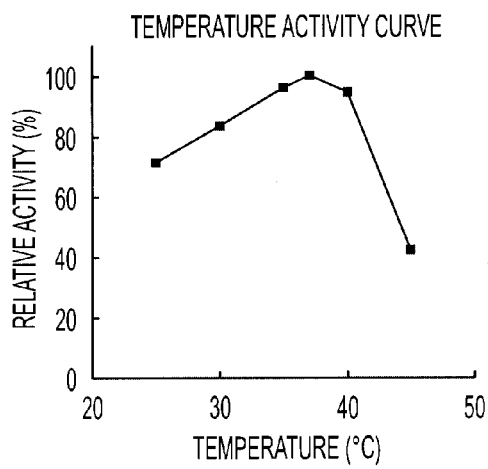
Figure 10:
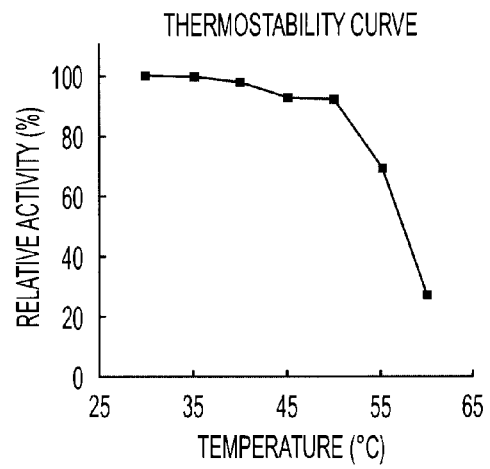
Figure 11:
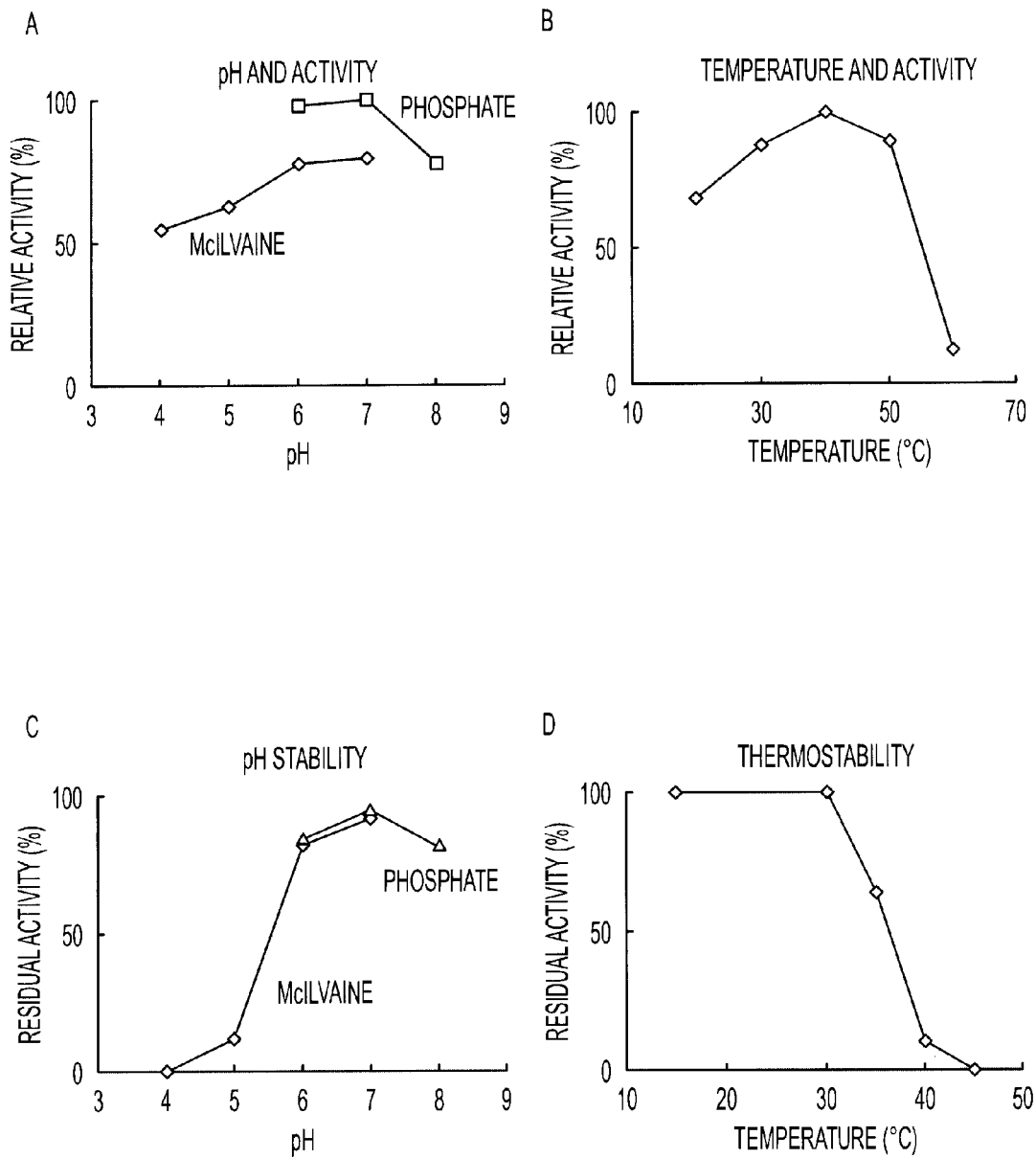
FIG. 11A-11D are graphs showing different characteristics of Lipase R.
Figure 12:
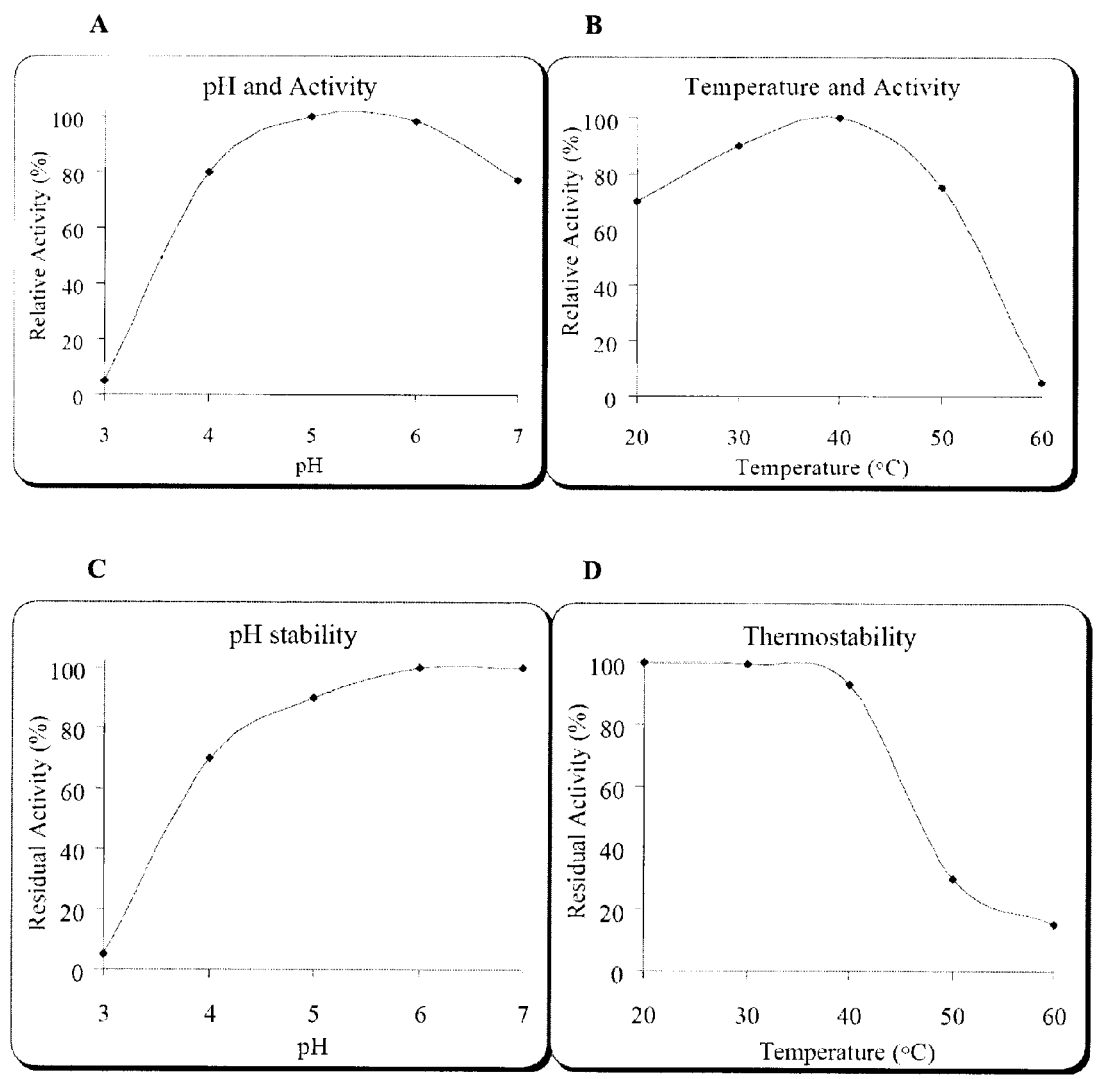
FIG. 12A-12D are graphs showing different characteristics of Lipase G50.

The sample volume used was 1 μl. Each sample was injected five times, cycling through all three samples (i.e., A, B, C, instead of A, A, A) so as not to bias the results by allowing one sample to sit untouched longer than the others. After each sample was run, the areas for each FAME peak (retention times previously determined) were entered into an Excel spreadsheet. Using the internal standards for conversion factors, the concentration of each free fatty acid in mmol/kg was calculated. Results of the gas chromatography analysis are shown below in Table 4 and FIG. 3. The average concentration of each fatty acid is represented in mmol/kg.

TABLE 4

Average concentration of fatty acid for each EMC (mmol/kg)

| Fatty Acid | FA Conc. CHEESEMAX ® treated EMC (mmol/kg) | FA Conc. CHEESEMAX ® + BIOLACTA ™ treated EMC (mmol/kg) |
| --- | --- | --- |
| C4 | 8.19 | 7.43 |
| C6 | 7.40 | 7.08 |
| C8 | 3.25 | 2.52 |
| C10 | 3.77 | 2.70 |
| C12 | 3.74 | 2.54 |
| C14 | 9.27 | 6.33 |
| C16 | 24.65 | 16.35 |
| C18 | 30.40 | 19.12 |

These results show that treatment of EMC with lipase and lactase in accordance with the methods described herein reduced the concentration of C18 fatty acids to 63% of that found in EMC treated with lipase only, while maintaining the concentration of C4 fatty acids to 91% of that of that found in EMC treated with lipase only.

One of the problems with analyzing the free fatty acid content of cheese is that the short chain fatty acids, the ones that provide cheese flavor, are volatile and are easily lost during the extraction and methyl esterification procedure. Previous unpublished work by the inventor has shown that when a measured amount of butyric acid is added to stock EMC, on average, as much as 40% of the added butyric acid is lost. Thus, it is not unreasonable to assume that a similar proportion of butyric acid native to EMC is lost during the extraction and methyl esterification procedures outlined above. In this experiment, the CHEESEMAX® treated EMC had a measured C4 concentration of 8.19 mmol and the CHEESEMAX®+BIOLACTA™ treated EMC had a measured C4 concentration of 7.43 mmol C4/kg. The true concentrations of C4 in these samples may be as high as 11.47 mmol/kg and 10.40 mmol/kg, respectively, based on previous studies of this phenomenon.

EXAMPLE 5

Evaluation of Five Different Lipases with BIOLACTA™

To test the effects of BIOLACTA™ with different lipases, EMC was made with five different lipases: Lipase A12, Lipase DF15, Lipase G50, Lipase M, and Lipase R. In each experiment, EMC was produced using the lipase both by itself and in conjunction with BIOLACTA™. After the EMC was produced, the free fatty acids were extracted, converted to methyl esters, and analyzed by gas chromatography. Samples of EMC were also tasted and rated on their cheesiness, sharpness, and soapiness.

A. EMC Production

Samples of BIOLACTA™, Lipase A12, Lipase DF15, Lipase G50, Lipase M, and Lipase R, were obtained directly from Amano Enzyme USA. All enzymes were used as a 100 mg/ml solution.

Several batches of Weyauwega Star Dairy Cheddar Cheese Curd with various Sell By dates were purchased from a local grocery store. Valeric acid (C5), an internal standard, was purchased from Aldrich (catalog number 240370); heptadecanoic acid (C17) was purchased from Sigma (H3500).

Each lipase was used with a different batch of EMC. For each batch, about 175 grams of the cheddar cheese curd was weighed into a Cusinart. An equal volume of buffer (0.5% w/v lactose, 1.0% w/v NaCl, and 1.5% w/v sodium citrate) was gradually added as the curds were processed into a slurry. Six 50 g aliquots of the slurry were weighed into sterile polycarbonate flasks, and the samples were then pasteurized for 30 minutes in boiling water. The samples were allowed to cool for at least 1 hour at the optimum working temperature of the lipase being used. The temperature used for each lipase is shown below in Table 5.

TABLE 5

Optimum working temperatures of lipases

| Lipase | Temperature (° C.) |
| --- | --- |
| Lipase A12 | 50 |
| Lipase DF15 | 40 |
| Lipase G50 | 40 |
| Lipase M | 40 |
| Lipase R | 30 |

All samples were dosed with 2 ml (0.2 g) of the lipase. Three of these samples were also dosed with 1.0 ml (0.1 g) of the BIOLACTA™ solution; the remaining three were left alone as a control. All of the samples were allowed to incubate at the working temperature of the lipase and 200 RPM overnight (between 17-22 hr). At the end of that time, they were placed in a boiling water bath for 30 minutes to inactivate the enzymes. After the EMCs were allowed to cool slightly, they were homogenized for one minute with a Polytron PT 1200 E handheld homogenizer at maximum RPM. A small (1.05 g) sample was taken for free fatty acid extraction and analysis (described below). The EMCs were then stored in the refrigerator and allowed to cool before the taste test.

B. Taste Test

For all lipases, 2 g each of one EMC sample treated only with the lipase and one EMC sample treated with both the lipase and BIOLACTA™ was mixed with 8 g of pasteurized cheese spread. The pasteurized cheese spread was also tasted by itself to establish base levels of flavors. Each sample was rated from 0-10 (with 10 being the highest score possible) by a single taster on cheesiness, sharpness, and lack of soapiness.

Table 6 below shows the results of the taste tests. In all taste tests, the control cheese was rated 1 (worst) on cheesiness and sharpness and 10 (best) on lack of soapiness.

TABLE 6

Taste Test Results

| Sample | Cheesiness | Sharpness | Lack of Soapiness | Total Score |
| --- | --- | --- | --- | --- |
| Control Cheese Spread | 1 | 1 | 10 | 12 |
| Lipase A12 Only | 1 | 1 | 9 | 11 |
| Lipase A12/ BIOLACTA™ | 1 | 1 | 8 | 10 |
| Lipase DF15 Only | 0 | 1 | 6 | 7 |
| Lipase DF15/ BIOLACTA™ | 0 | 1 | 5 | 6 |
| Lipase G50 Only | 1 | 2 | 10 | 13 |
| Lipase G50/BIOLACTA™ | 2 | 3 | 9 | 14 |
| Lipase M Only | 1 | 2 | 6 | 9 |
| Lipase M/BIOLACTA™ | 2 | 2 | 8 | 12 |
| Lipase R Only | 2 | 2 | 7 | 11 |
| Lipase R/BIOLACTA™ | 4 | 3 | 9 | 16 |

In addition to the taste characteristics noted above, bitterness was also detected in the EMC samples made with Lipase M. The sample prepared with Lipase M only had a bitterness level of 4 (or 6 for lack of bitterness), while the sample prepared with both Lipase M and BIOLACTA™ had a bitterness level of 2 (or 8 for lack of bitterness). All of the other EMCs would have bitterness levels of 0 (or 10 for lack of bitterness).

The foregoing results show that the use of different lipases with BIOLACTA™ can have different effects on cheesiness, sharpness and lack of soapiness. Thus, EMCs with a desired flavor profile can be obtained by selecting a lipase/lactase combination that achieves the desired effect.

C. Free Fatty Acid Extraction and Conversion to Methyl Esters

Approximately 1.05 g of each EMC was weighed into a 50 ml centrifuge tube. The following reagents were added to each tube: 1 ml 2.5 M $H_2SO_4$, 3 ml water, and 5 ml internal standard (C5 and C17, 1 mg/ml of each fatty acid in 1:1 ether:hexane). The samples were vigorously vortexed to create emulsions. The samples were centrifuged for 15-30 minutes at 3000 RPM in a Beckman Coulter Allegra™ 25R Centrifuge, System ID 433500. The oil layers were drawn off with a pipette and allowed to pass through SEP columns equilibrated with 10 ml heptane. The columns were washed with 10 ml 2:1 chloroform: propanol, and the free fatty acids (FFA) were eluted with 5 ml 2% formic acid in ether. One ml of each elution was transferred to a capped glass tube and mixed with 0.2 ml 2,2-dimethoxypropane (Sigma, reagent grade 98%, D136808), 0.2 ml 1.5 M HCl in MeOH (Fluka, 17935), and 0.6 ml anhydrous methanol (Sigma, 322415). The samples were allowed to stand overnight at room temperature before being analyzed on the gas chromatograph.

D. Gas Chromatography Analysis

The samples were run on a gas chromatograph system, Model 6890, manufactured by Aglient Technologies, with a split/splitless inlet, a split liner, and a pulsed split inlet model. The split ratio was 50:1 and the split flow 109 ml/min. The inlet temperature was 250° C., and the head pressure was 230 kPa. The column used was 0.15 um DB-23, 60 m×0.25 mm ID. The total gas flow was 113 ml/min, and the carrier gas was helium. Helium flow was 2.2 ml/min, helium make-up flow was 30 ml/min, hydrogen flow was 40 ml/min, and air was 800 ml/min. The average velocity was 34 cm/sec. The oven was programmed as shown below in Table 7, with the detector temperature set at 280° C.

TABLE 7

Oven Program for FAME Analysis

| Temperature (° C.) | Rate (° C./min) | Final Temperature (° C.) | Hold Time (minutes) |
|---|---|---|---|
| 50 | N/A | 50 | 4 |
| 50 | 25 | 175 | 0 |
| 175 | 4 | 230 | 0 |

The sample volume used was 1 μl. Each sample was injected three times, cycling through all six samples (i.e., A, B, C, instead of A, A, A) so as not to bias the results by allowing one sample to sit untouched longer than the others. The concentration of each free fatty acid in mmol/kg was calculated using the internal standards for conversion factors,.

Table 8 shows the results of the gas chromatography analysis. Concentrations of free fatty acids that contribute to cheesy flavor (C4) or soapy flavor (C14, C16, and C18) in the EMCs produced with the various lipases are shown:

TABLE 8

Average Free Fatty Acid Concentration Levels in EMCs Made with Various Lipases

| Sample | Average C4 Conc. (mmol/kg) | Average C14 Conc. (mmol/kg) | Average C16 Conc. (mmol/kg) | Average C18 Conc. (mmol/kg) |
|---|---|---|---|---|
| Lipase A12 Only | 1.2 | 2.93 | 8.9 | 5.3 |
| Lipase A12/BIOLACTA ™ | 1.37 | 6.2 | 20.17 | 10.83 |
| Lipase DF15 Only | 28.1 | 22.67 | 48.83 | 18.5 |
| Lipase DF15/BIOLACTA ™ | 24.23 | 18.73 | 42.5 | 15.1 |
| Lipase G50 Only | 0.59 | 1.0 | 2.87 | 1.13 |
| Lipase G50/BIOLACTA ™ | 0.73 | 1.17 | 3.4 | 1.3 |
| Lipase M Only | 14.67 | 14.67 | 38.33 | 17.0 |
| Lipase M/BIOLACTA ™ | 10.67 | 14.0 | 36.33 | 16.33 |
| Lipase R Only | 6.53 | 3.77 | 9.63 | 5.5 |
| Lipase R/BIOLACTA ™ | 6.9 | 6.5 | 16.7 | 10.6 |

Three of the five lipases used in this experiment did not produce much, if any, free fatty acid in the EMC samples. For three of the lipases (Lipase A12, Lipase G50, and Lipase R), concentrations of C4 were much lower than they were previously found in EMC made with CHEESEMAX® (8.19 mmol/kg when CHEESEMAX® was used by itself and 7.43 mmol/kg with both CHEESEMAX® and BIOLACTA™; see Table 4, above). The concentrations of long chain fatty acid such as C14, C16, and C18 produced by these lipases were also much lower than produced in CHEESEMAX® EMC (30.4 mmol/kg) or CHEESEMAX®/BIOLACTA™ EMC (19.12 mmol/kg) (see Table 4).

In the experiment described above, Lipase A12 did not improve the taste of EMC relative to the control; however, both Lipase G50 and Lipase R produced improvements in cheesiness and sharpness. Thus, the determined free fatty acid concentrations are not entirely consistent with the taste test results. It is possible that side reactions are affecting the determined free fatty acid concentrations or taste test results, or both. Moreover, the taste test results reported above were based on a single tasting by a single person, and so additional tasting by other people might produce results more consistent with the free fatty acid concentrations.

Two of the lipases, Lipase DF15 and Lipase M, produced C4 concentrations that are higher than those found in CHEESEMAX® EMC. However, in taste tests, those EMCs (both lipase EMC and lipase/BIOLACTA™ EMC) scored very low on cheesiness and sharpness, being comparable to or lower than the control cheese spread. Both EMCs made with Lipase DF15 scored lowest on lack of soapiness (for high soapiness), so it is possible that soapiness may have masked any cheesy flavor present in the sample. The Lipase M EMCs also scored low on lack of soapiness, though not as low as the Lipase DF15 EMCs. Thus, for these enzymes as well, the determined free fatty acid concentrations are not entirely consistent with the taste test results.

Table 9 shows the ratios of long chain fatty acid in lipase+BIOLACTA™ EMC to the long chain fatty acid concentrations in the corresponding lipase EMC. For comparison, the ratios for CHEESEMAX® are also presented. A ratio of less than one indicates that the use of the lipase/lactase combination reduced the long chain fatty acid content as compared to use of the lipase alone.

TABLE 9

Long Chain Fatty Acid Ratios of Lipase/BIOLACTA ™ EMC to Lipase EMC

| Lipase | C14 Ratio | C16 Ratio | C18 Ratio | Average Ratio |
|---|---|---|---|---|
| CHEESEMAX ® | 0.68 | 0.66 | 0.63 | 0.66 |
| Lipase A12 | 2.12 | 2.27 | 2.04 | 2.14 |
| Lipase DF15 | 0.83 | 0.87 | 0.82 | 0.84 |
| Lipase G50 | 1.17 | 1.18 | 1.15 | 1.17 |
| Lipase M | 0.95 | 0.95 | 0.96 | 0.95 |
| Lipase R | 1.70 | 1.73 | 1.93 | 1.79 |

For all lipases, including CHEESEMAX®, the ratio was about the same for each free fatty acid (C14, C16, C18). However, none of the lipases produced a ratio as low as that produced by CHEESEMAX® (average ratio 0.66). For Lipase A12, adding BIOLACTA™ to the EMC produced more than twice the long chain fatty acid (ratio 2.14), even though the Lipase A12/BIOLACTA™ EMC tasted less soapy than the Lipase A12 EMC. Combining BIOLACTA™ with Lipase DF15 produced less long chain fatty acid (average ratio 0.84) but slightly more soapy flavor during the taste test. The EMC made with Lipase G50/BIOLACTA™ had slightly higher long chain fatty acid concentrations (average ratio 1.17) and a slightly more soapy taste. For Lipase M, adding BIOLACTA™ to the EMC reduced concentrations of all free fatty acid slightly (average ratio 0.95), but C4 was affected more strongly than the long chain fatty acid. As noted above, the Lipase M/BIOLACTA™ EMC had slightly less soapy flavor than the Lipase M EMC. For Lipase R, the C4 concentrations were slightly higher in the Lipase R/BIOLACTA™ EMC, but the long chain fatty acid concentrations were increased to a greater degree (average ratio 1.79). The Lipase R/BIOLACTA™ EMC scored better in all categories during the taste test than the Lipase R EMC. Thus, for three of the lipases, taste test results were not consistent with the gas chromatography results.

Of the five lipases examined in this experiment, three of them (Lipase A12, Lipase G50, and Lipase R) produced more long chain fatty acid when combined with BIOLACTA™ during EMC production. Two lipases, Lipase DF15 and Lipase M, produced lower long chain fatty acid concentrations when combined with BIOLACTA™.

The foregoing illustrate how different combinations of lipase(s) and lactase(s) can be screened for a desired effect on EMC, such as a desired effect on one or more of free fatty acid content, cheesiness, sharpness, lack of soapiness, and aroma.

What is claimed is:

1. A method of preparing a cheese product comprising (a) contacting a cheese composition comprising lipids and lactose with a purified lactose or a composition comprising a purified lactose, and subsequently, (b) contacting the cheese composition with one or more lipases and one or more lactases, wherein at least one of the one or more lipases preferentially hydrolyzes short chain fatty acids before hydrolyzing long chain fatty acids, and wherein at least one of the one or more lactases exhibits galactose transferring activity, and wherein the cheese product has a stronger cheese flavor and/or less of a soapy flavor associated with reduced palmitic acid or stearic acid levels than a comparable product treated with the one or more lipases but not the one or more lactases.

2. The method of claim 1, further comprising an enzyme inactivation step.

3. The method of claim 1, wherein the cheese product has a higher ratio of free short chain fatty acids to free long chain fatty acids than a comparable product treated with the one or more lipases but not the one or more lactases.

4. The method of claim 1, wherein the cheese product is a cheese product selected from enzyme modified cheese and natural cheese.

5. The method of claim 1, wherein the cheese product is a final cheese product.

6. The method of claim 1, wherein the cheese product is a food additive.

7. The method of claim 1, wherein the lipase comprises a lipase EC 3.1.1.3 produced by *Rhizopus oryzae* fermentation.

8. The method of claim 1, wherein the lipase comprises a lipase EC 3.1.1.3 produced by *Mucor javanicus* fermentation.

9. The method of claim 1, wherein the lactase comprises β-galactosidase EC 3.2.1.23 produced by *Bacillus circulans* fermentation.

10. The method of claim 1, wherein the lipase comprises a lipase EC 3.1.1.3 produced by *Rhizopus oryzae* fermentation, and wherein the lactase comprises β-galactosidase EC 3.2.1.23 produced by *Bacillus circulans* fermentation.

11. The method of claim 1, wherein the lipase comprises a lipase EC 3.1.1.3 produced by *Mucor javanicus* fermentation, and wherein the lactase comprises β-galactosidase EC 3.2.1.23 produced by *Bacillus circulans* fermentation.

12. The method of claim 1, wherein the lipase comprises a lipase selected from the group consisting of a lipase EC 3.1.1.3 produced by *Aspergillus niger* fermentation, a lipase EC 3.1.1.3 produced by *Rhizopus oryzae* fermentation, a lipase EC 3.1.1.3 produced by *Penicillium camemberti* fermentation, and a lipase EC 3.1.1.3 produced by *Penicillium roqueforti* fermentation.

13. The method of claim 1, wherein the lipase comprises a lipase selected from the group consisting of a lipase EC 3.1.1.3 produced by *Aspergillus niger* fermentation, a lipase EC 3.1.1.3 produced by *Rhizopus oryzae* fermentation, a lipase EC 3.1.1.3 produced by *Penicillium camemberti* fermentation, and a lipase EC 3.1.1.3 produced by *Penicillium roqueforti* fermentation, and wherein the lactase comprises β-galactosidase EC 3.2.1.23 produced by *Bacillus circulans* fermentation.

* * * * *